United States Patent
Delgado

(10) Patent No.: US 9,188,544 B2
(45) Date of Patent: Nov. 17, 2015

(54) PROTECTIVE FLUORINE-DOPED SILICON OXIDE FILM FOR OPTICAL COMPONENTS

(71) Applicant: KLA-Tencor Corporation, Milpitas, CA (US)

(72) Inventor: Gildardo Delgado, Livermore, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 15 days.

(21) Appl. No.: 13/855,475

(22) Filed: Apr. 2, 2013

(65) Prior Publication Data

US 2013/0265572 A1    Oct. 10, 2013

Related U.S. Application Data

(60) Provisional application No. 61/620,299, filed on Apr. 4, 2012.

(51) Int. Cl.
G01N 21/88 (2006.01)
G02B 1/11 (2015.01)
G01N 21/95 (2006.01)
G01N 21/956 (2006.01)
(Continued)

(52) U.S. Cl.
CPC ........ G01N 21/8806 (2013.01); G01N 21/9501 (2013.01); G01N 21/956 (2013.01); G02B 1/105 (2013.01); G02B 1/11 (2013.01); G02B 1/113 (2013.01); H01L 31/02168 (2013.01); G01N 2021/95676 (2013.01); G02B 7/16 (2013.01); Y02E 10/50 (2013.01)

(58) Field of Classification Search
USPC .......... 438/482, 485, 636, 766, 778; 257/347, 257/638, 645, 651; 427/255.37, 255.39, 427/255.17
See application file for complete search history.

(56) References Cited

U.S. PATENT DOCUMENTS 5,563,702 A    10/1996    Emery et al.
5,965,918 A *  10/1999    Ono .............................. 257/347
(Continued)

FOREIGN PATENT DOCUMENTS

EP    1341221 A1    9/2003
JP    5-215929    8/1993
(Continued)

OTHER PUBLICATIONS

Attia, S. M. et al. "Review on Sol-Gel Derived Coatings: Process, Techniques and Optical Applications", J. Mater. Sci. Technol., vol. 18, No. 3, 2002, pp. 211-218.
(Continued)

Primary Examiner — Sang Nguyen
(74) Attorney, Agent, or Firm — Bever, Hoffman & Harms, LLP

(57) ABSTRACT

An optical component includes a substrate and a fluorine-doped thin film formed on the substrate. This fluorine-doped thin film is dense, and thus very low absorbing and insensitive to various vacuum, temperature, and humidity conditions. This dense film has a high refractive index, which remains stable irrespective of environmental conditions. The fluorine-doped thin film can advantageously ensure low scattering, low reflectance, and high transmittance. Moreover, the fluorine-doped thin film is damage resistant to incident radiation density. The fluorine-doped thin film may be a fluorine-doped silicon oxide film having a thickness of approximately 1-10 nm and a fluorine concentration of 0.1% to 5%.

12 Claims, 17 Drawing Sheets

(51) Int. Cl.
*G02B 1/10* (2015.01)
*G02B 1/113* (2015.01)
*H01L 31/0216* (2014.01)
*G02B 7/16* (2006.01)

(56) References Cited

U.S. PATENT DOCUMENTS

| | | | |
|---|---|---|---|
| 6,149,976 A * | 11/2000 | Matsuki et al. | 427/255.37 |
| 6,201,601 B1 | 3/2001 | Vaez-Iravani et al. | |
| 6,271,916 B1 | 8/2001 | Marxer et al. | |
| 6,300,672 B1 | 10/2001 | Lee | |
| 6,456,361 B1 | 9/2002 | Suzuki | |
| 6,518,646 B1 * | 2/2003 | Hopper et al. | 257/642 |
| 6,797,649 B2 | 9/2004 | Scherer et al. | |
| 6,872,479 B2 | 3/2005 | Maier et al. | |
| 7,128,984 B2 | 10/2006 | Maier et al. | |
| 7,352,457 B2 | 4/2008 | Kvamme et al. | |
| 7,525,649 B1 | 4/2009 | Leong et al. | |
| 7,964,522 B2 | 6/2011 | Moore et al. | |
| 2001/0003060 A1 * | 6/2001 | Yokohama et al. | 438/622 |
| 2002/0011675 A1 * | 1/2002 | Oda et al. | 257/776 |
| 2002/0021432 A1 | 2/2002 | Suzuki et al. | |
| 2002/0037655 A1 * | 3/2002 | Hasunuma et al. | 438/778 |
| 2003/0197849 A1 | 10/2003 | Ishikawa et al. | |
| 2004/0092131 A1 * | 5/2004 | Scherer et al. | 438/766 |
| 2004/0214426 A1 * | 10/2004 | Sakai | 438/636 |
| 2005/0025882 A1 | 2/2005 | Partlo et al. | |
| 2005/0287771 A1 * | 12/2005 | Seamons et al. | 438/482 |
| 2006/0023311 A1 * | 2/2006 | Scherer et al. | 359/603 |
| 2006/0170889 A1 | 8/2006 | Honda | |
| 2007/0002465 A1 | 1/2007 | Chuang et al. | |
| 2009/0180176 A1 | 7/2009 | Armstrong et al. | |
| 2009/0214801 A1 * | 8/2009 | Higashi et al. | 427/579 |
| 2009/0286348 A1 * | 11/2009 | Mouli | 438/73 |
| 2013/0003158 A1 * | 1/2013 | Gousev et al. | 359/290 |
| 2013/0017205 A1 | 1/2013 | Giaccia et al. | |

FOREIGN PATENT DOCUMENTS

| | | | |
|---|---|---|---|
| JP | 7-147447 A | | 6/1995 |
| JP | 08115976 A | * | 5/1996 |

OTHER PUBLICATIONS

Gaur, A. M. et al. "Deposition of Doped TiO2 Thin Film by Sol Gel Technique and its Characterization: A Review", Proceedings of the World Congress on Engineering 2011, vol. II, WCE 2011, Jul. 6-8, 2011, London, U.K., 4 pgs.

Lawrence Livermore National Laboratory, "Optical Coatings by the Sol-Gel Process", Energy and Technology Review, Oct. 1985, pp. 8-14.

Malinowski, M. et al. "Controlling Contamination in Mo/Si Multilayer Mirrors by Si Surface-capping Modifications", Proc. SPIE, vol. 4688, Emerging Lithographic Technologies VI, Jul. 5, 2002, pp. 442-453.

Protopapa, M. L. et al. "Laser-induced damage measurements on phase-unifying mirrors for XeF excimer laser cavities", Proc. of SPIE, vol. 5250, Advances in Optical Thin Films, Feb. 25, 2004, pp. 656-662.

Temple, P. A. "Measurement of thin-film optical absorption at the air-film interface within the film and at the film-substrate interface", Appl. Phys. Lett., vol. 34, No. 10, May 15, 1979, pp. 677-679.

* cited by examiner

PROTECTIVE FLUORINE-DOPED SILICON OXIDE FILM FOR OPTICAL COMPONENTS

RELATED APPLICATIONS

This application claims priority to U.S. Provisional Patent Application 61/620,299, entitled "Protective F-Doped Silicon Oxide Layer For Optics And CCD/TDI Sensors For Actinic Inspection" filed Apr. 4, 2012.

BACKGROUND OF THE DISCLOSURE

Standard optical surfaces include anti-reflective coatings as well as other coatings for beam splitters, mirrors, charge-coupled devices (CCDs), detectors, and time delay integration (TDI) CCDs. Unfortunately, these coatings may be adversely affected by humidity, oxidation, contamination, radiation damage, and other environmental conditions. Specifically, various environmental conditions can deteriorate the coating performance or at least induce coating damage. Moreover, high fluence applications (i.e. where the total number of photons intersecting a unit area in a specific time interval is high) typically expose optical surfaces to radiation for long periods of time, which can exacerbate deterioration and damage of those coatings.

Various bulk materials have been suggested for protecting optical surfaces. One exemplary material suggesting for protecting optical surfaces used in UV (ultra-violet) 193 nm and 157 nm applications is fluorine-doped silica glass. FIG. 1 illustrates an exemplary process for manufacturing a protective layer from fused silica. This process uses a precursor material 101 of high purity fused silica. A natural silica precursor is typically melted in a furnace, either electrically or with a $H_2/O_2$ flame, and then grown to form ingots or large bulk material. A synthetic fused silica is made from a silicon-rich chemical precursor using, for example, a continuous flame hydrolysis process. This process includes the chemical gasification of silicon, the oxidation of this gas to silicon oxide, and the thermal fusion of the resulting dust. Yet another fused silica can be formed by adding silicon tetrachloride to a hydrogen-oxygen flame.

In step 102, the precursor material can be melted (or processed) and then doped with fluorine to form large bulk structures (e.g. ingots). In step 103, the bulk structures can be cut into rough shapes depending on their final application. In step 104, the shapes are ground to a rough surface finish. In step 105, the material is polished to a final RMS (a standard industry surface roughness measured in microinches) roughness to meet optical specification.

The resulting optical elements (called lens, filters, pellicles, covers, layers, etc. in the industry) can provide protection from environmental conditions and offer long term high radiation resistance. However, their manufacture for use with specific optical components having custom sizes and shapes is time- and labor-intensive, thereby making the protected optical components more expensive.

Therefore, a need arises for a way to protect optical components from environmental conditions and to ensure long term high radiation resistance at minimum expense.

SUMMARY

An optical component operable with deep ultraviolet (DUV) radiation, vacuum ultraviolet (VUV) radiation, extreme ultraviolet (EUV) radiation, and/or charged particles is described. This optical component includes a substrate and a fluorine-doped silicon oxide film formed on the substrate. The fluorine-doped silicon oxide film has a thickness of approximately 1-10 nm and has a fluorine concentration of 0.1% to 5%. In one embodiment, the fluorine-doped silicon oxide film can be an anti-reflective coating (ARC) for the optical component.

This fluorine-doped thin film is dense and thus very low absorbing. For example, this dense film is highly resistant to both atomic hydrogen (H) as well as hydrogen gas $H_2$. This fluorine-doped thin film is insensitive to various vacuum, temperature, and humidity conditions. This dense coating remains stable irrespective of environmental conditions. The fluorine-doped thin film can advantageously ensure low scattering, low reflectance, and high transmittance. Moreover, the fluorine-doped thin film is damage resistant to incident radiation density. This thin film can be easily adhered to state-of-the-art materials used for optical components, such as boron, silicon nitride, rhodium, titanium oxide, ruthenium, niobium oxide, and silicon oxide. The fluorine-doped thin film also has a hardness of greater than 6.5 GPa (as calculated by indentation depth) and or Young's modulus of greater than 60 GPa (with nanoindentation method), thereby making it rugged in actual use.

A method of fabricating a protective film for an optical component is described. This method includes performing a thin film deposition on a silicon substrate to form an oxide, and introducing fluorine as a dopant during the thin film deposition, thereby generating the fluorine-doped silicon oxide film. The fluorine may be a fluorine gas or atomic fluorine, e.g. from dissociating fluorine gas or a fluorine precursor to generate the atomic fluorine. Performing thin film deposition may include oxidation, deep ultraviolet (DUV) oxidation, ion-assisted deposition, ion beam sputtering, chemical vapor deposition (CVD), plasma enhanced CVD, plasma deposition, thermal evaporation, or electron beam evaporation.

An electron-bombarded image sensor is described. This electron-bombarded image sensor includes an evacuated housing including a window, a photocathode, and an image sensor. The photocathode and the image sensor are positioned inside the evacuated housing. At least one of the window and the image sensor includes a fluorine-doped silicon oxide film, the fluorine-doped silicon oxide film having a thickness of approximately 1-10 nm and having a fluorine concentration of 0.1% to 5%. The image sensor can further include a silicon oxide layer formed on top of a boron layer or between a boron layer and the fluorine-doped silicon oxide film.

A catadioptric imaging system is also described. This catadioptric imaging system includes a laser, adaptation optics, an objective, and a prism. The adaptation optics can receive an illumination beam of the laser and controlling an illumination beam size and profile on a sample being inspected. The objective may include a catadioptric objective, a focusing lens group, and a zooming tube lens section. The prism can direct light from the laser along an optical axis at normal incidence to a surface of the sample and direct specular reflections from surface features of the sample as well as reflections from optical surfaces of the objective along an optical path to an imaging plane. At least one component of the adaptation optics, the objective, and the imaging plane includes a fluorine-doped silicon oxide film, the fluorine-doped silicon oxide film having a thickness of approximately 1-10 nm and having a fluorine concentration of 0.1% to 5%.

A surface inspection apparatus is also described. The surface inspection apparatus includes a laser system for generating a beam of radiation. An illumination system can focus the beam of radiation at a non-normal incidence angle relative to a surface to form an illumination line on the surface substantially in a plane of incidence of the focused beam, wherein the plane of incidence is defined by the focused beam and a direction that is through the focused beam and normal to the surface. A collection system can image the illumination line, wherein the collection system includes an imaging lens for collecting light scattered from a region of the surface comprising the illumination line. A focusing lens can focus the collected light. A device can include an array of light sensitive elements, wherein each light sensitive element of the array of light sensitive elements can detect a corresponding portion of a magnified image of the illumination line. At least one component of the illumination system, the collection system, and the array of light sensitive elements includes a fluorine-doped silicon oxide film, the fluorine-doped silicon oxide film having a thickness of approximately 1-10 nm and having a fluorine concentration of 0.1% to 5%.

An inspection system is also described. This inspection system includes an illumination source and optics arranged to direct and focus radiation from the illumination source onto a sample. A first detector can detect light scattered by first size particles on a surface of the sample. A second detector can detect light scattered by second size particles on the surface of the sample. At least one component of the optics, the first detector, and the second detector includes a fluorine-doped silicon oxide film, the fluorine-doped silicon oxide film having a thickness of approximately 1-10 nm and having a fluorine concentration of 0.1% to 5%.

An optical system for detecting anomalies of a sample is also described. The optical system includes a laser system for generating a first beam and a second beam. First optics can direct the first beam along a first path onto a first spot on a surface of the sample. Second optics can direct the second beam along a second path onto a second spot on the surface of the sample, wherein the first and second paths are at different angles of incidence to the surface of the sample. Collection optics can include a curved mirrored surface for receiving scattered radiation from the first spot or the second spot and focusing the scattered radiation to a detector. The detector can provide a single output value in response to radiation focused onto it by the curved mirrored surface. An instrument can cause relative motion between the first and second beams and the sample so that the first and second spots are scanned across the surface of the sample. At least one optical component of the first optics, the second optics, the detector, and the collection optics includes a fluorine-doped silicon oxide film, the fluorine-doped silicon oxide film having a thickness of approximately 1-10 nm and having a fluorine concentration of 0.1% to 5%.

A dark-field inspection system is also described. This dark-field inspection system includes illumination optics for directing light to a sample being inspected. An optical collection subsystem can collect scattered light from the sample and direct collected light. A first imaging sensor can receive a first portion of the collected light associated with low light scattering. A second imaging sensor can receive a second portion of the collected light associated with high light scattering. At least one optical component of the illumination optics, the optical collection subsystem, the first imaging sensor, and the second imaging sensor includes a fluorine-doped silicon oxide film, the fluorine-doped silicon oxide film having a thickness of approximately 1-10 nm and having a fluorine concentration of 0.1% to 5%.

An inspection system is also described. This inspection system includes a pulsed illumination source, an image sensor, and optical components. The image sensor can include an electron-bombarded charge-coupled device (EBCCD) detector. The optical components can direct pulsed illumination from the pulsed illumination source to a continuously moving object, and direct reflected light from the object to the image sensor. The window of the EBCCD or at least one of the optical components includes a fluorine-doped silicon oxide film, the fluorine-doped silicon oxide film having a thickness of approximately 1-10 nm and having a fluorine concentration of 0.1% to 5%. The inspection system may include a processor configured to operate the image sensor, e.g. performing timed delay integration (TDI) during an illumination pulse, and performing split-readout during non-illumination.

An optical inspection system for inspecting a surface of a photomask, reticle, or semiconductor wafer for defects is also described. This optical inspection system can include a light source for emitting an incident light beam along an optical axis. An optical system is disposed along the optical axis and includes a plurality of optical components for directing the incident light beam to the surface, the optical system being capable of scanning the surface. A transmitted light detector arrangement can include transmitted light detectors, which are arranged for sensing a light intensity of transmitted light. A reflected light detector arrangement can include reflected light detectors, which are arranged for sensing a light intensity of reflected light. At least one component of the optical system, the transmitted light detector arrangement, and the reflected light detector arrangement includes a fluorine-doped silicon oxide film, the fluorine-doped silicon oxide film having a thickness of approximately 1-10 nm and having a fluorine concentration of 0.1% to 5%.

A system for inspecting a sample is also described. This system includes an illumination source for illuminating the sample. Image relay optics can direct light outputs, the light outputs being reflections or transmissions, of the sample to a first channel image mode relay when the light outputs correspond to a first channel, and to a second channel image mode relay when the light outputs correspond to a second channel. A sensor can receive relay outputs of the first channel image mode relay and the second channel image mode relay. At least one component of the image relay optics and the sensor can include a fluorine-doped silicon oxide film, the fluorine-doped silicon oxide film having a thickness of approximately 1-10 nm and having a fluorine concentration of 0.1% to 5%.

An inspection system for inspecting a surface of a sample is also described. The inspection system can include an illumination subsystem configured to produce a plurality of channels of light, each channel of light produced having differing characteristics from at least one other channel of light. Optics can be provided to receive the plurality of channels of light and combine the plurality of channels of light into a spatially separated combined light beam and direct the spatially separated combined light beam toward the sample. A data acquisition subsystem can include at least one detector configured to detect reflected light from the sample. The data acquisition subsystem is configured to separate the reflected light into a plurality of received channels corresponding to the plurality of channels of light. At least one optical component of the optics and the data acquisition subsystem includes a fluorine-doped silicon oxide film, the fluorine-doped silicon oxide film having a thickness of approximately 1-10 nm and having a fluorine concentration of 0.1% to 5%.

DETAILED DESCRIPTION OF THE DRAWINGS

In accordance with an improved method of protecting optical components, a fluorine-doped thin film can be provided. This fluorine-doped thin film is dense and thus very low absorbing. For example, this dense film is highly resistant to both atomic hydrogen (H) as well as hydrogen gas $H_2$. This fluorine-doped thin film is insensitive to various vacuum, temperature, and humidity conditions. This dense coating has a high refractive index, which remains stable irrespective of environmental conditions. The fluorine-doped thin film can advantageously ensure low scattering, low reflectance, and high transmittance. Moreover, the fluorine-doped thin film is damage resistant to incident radiation density. This thin film can be easily adhered to state-of-the-art materials used for optical components, such as boron, silicon nitride, silicon, rhodium, titanium oxide, niobium oxide, ruthenium, and silicon oxide. The fluorine-doped thin film also has a hardness of greater than 6.5 GPa (as calculated by indentation depth) and or Young's modulus of greater than 60 GPa (with nanoindentation method), thereby making it rugged in actual use.

Figure 1:
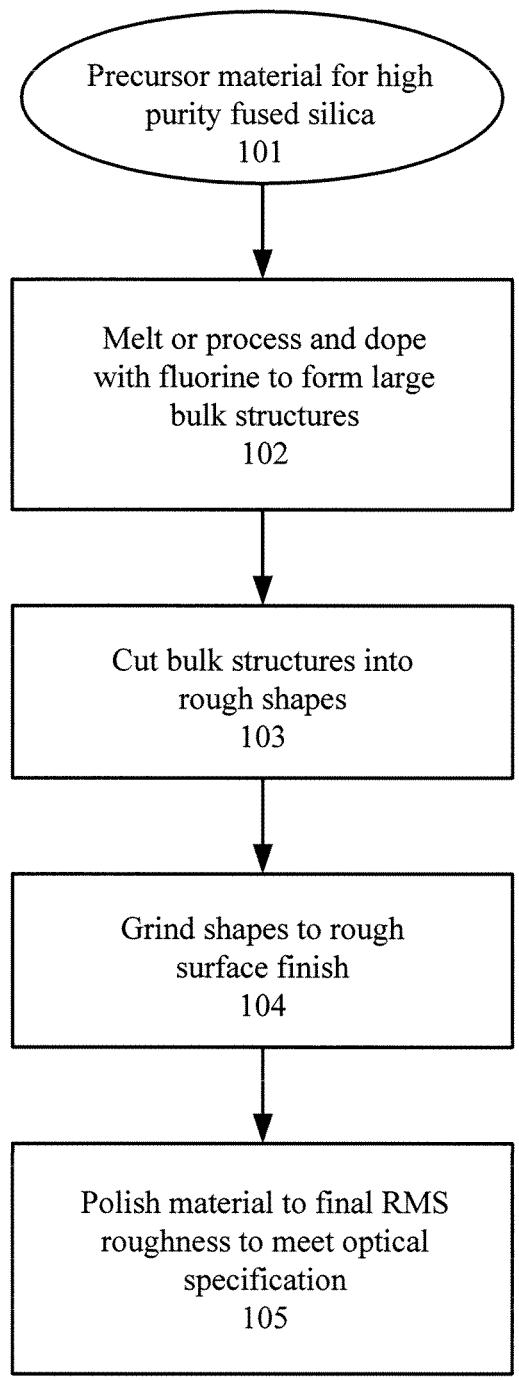
FIG. 1 illustrates an exemplary process for manufacturing a protective layer from fused silica.
Figure 2:
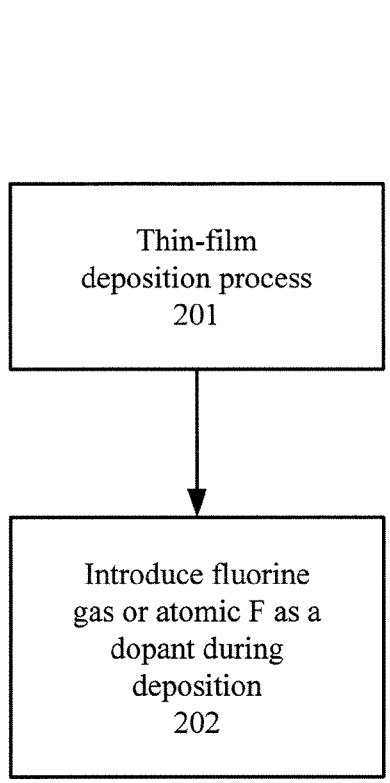
FIG. 2 illustrates a generic process for manufacturing a fluorine-doped thin film.

FIG. 2 illustrates a generic process for manufacturing a fluorine-doped thin film. In step 201, a thin-film deposition process can be performed. Exemplary thin-film depositions suitable for fluorine doping are described below. In step 202, fluorine gas $F_2$ or atomic F can be added as dopant during the thin-film deposition. In one embodiment, dissociated $F_2$ or another precursor can be used in step 202. Target values in the thin-film for fluorine range from approximately 0.1% to 5% by volume.

Figure 3:
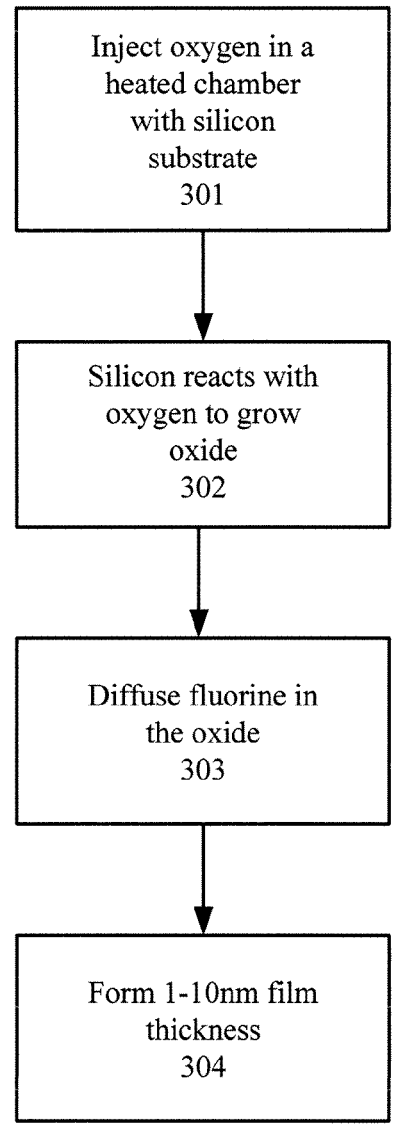
FIG. 3 illustrates an exemplary process for forming a fluorine-doped silicon oxide film using oxidation.

FIG. 3 illustrates an exemplary process for forming a fluorine-doped silicon oxide film using oxidation. In step 301, oxygen can be injected into a heated chamber with a silicon substrate. In one embodiment, the chamber can be heated in the range of approximately 800-1200° C. In one embodiment, oxygen gas ($O_2$) can be injected in the chamber. In another embodiment, $H_2O$ (water, steam) can be injected in the chamber. In step 302, the surface of the silicon substrate reacts with the oxygen, thereby growing a silicon oxide. In step 303, fluorine can be diffused in the chamber during the silicon oxide formation. In one embodiment, a fluorine gas $F_2$ can be diffused in the chamber. In another embodiment, atomic fluorine (F) (provided by disassociated $F_2$ or another precursor) can be diffused instead of fluorine gas. As a result of the diffusion, in step 304, a 1-10 nm thick fluorine-doped silicon oxide film can be formed. In one embodiment, this thickness can be achieved within 0.5 to 3 hours based on the temperature of the chamber in step 301, the reaction time in step 302, and the amount of fluorine diffused in step 303.

Figure 4:
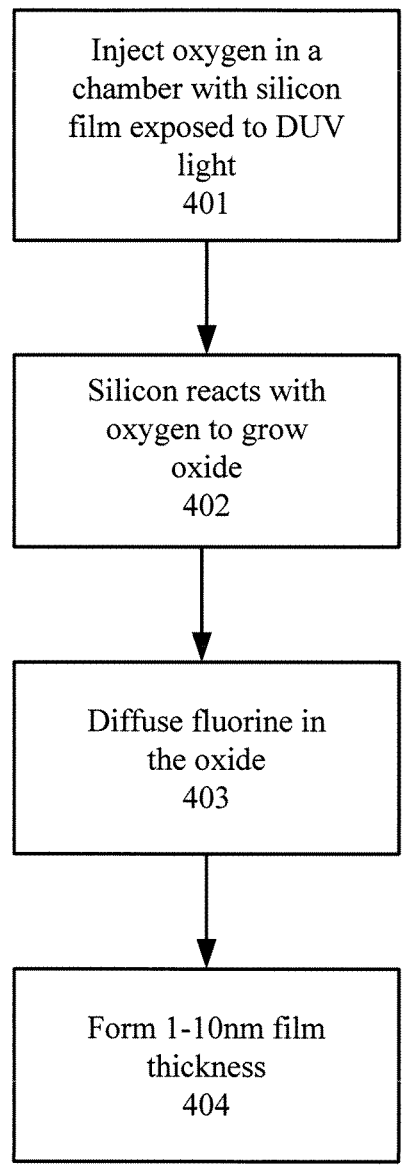
FIG. 4 illustrates an exemplary process for forming a fluorine-doped silicon oxide film using DUV (deep ultraviolet) oxidation.

FIG. 4 illustrates an exemplary process for forming a fluorine-doped silicon oxide film using DUV (deep ultraviolet) oxidation. In step 401, oxygen can be injected into a chamber with a silicon film exposed to DUV light. In one embodiment, the DUV light has a wavelength below 245 nm. The UV light source may include any UV light source known in the art. In one embodiment, the light source may include a narrow band source configured to generate UV light at one or more selected bands within the UV spectral region. For example, the light source may include one or more laser sources suitable for emitting ultraviolet light. The light source may include a broadband source configured to generate UV light at one or more selected bands within the UV spectral region. For example, the light source may include one or more broadband lamps suitable for emitting ultraviolet light. For instance, the broadband may include, but is not limited to, a mercury lamp or source can be 172 nm excimer lamp. It is noted herein that a mercury lamp may display multiple strong emission UV wavelengths, such as 165 nm, 185 nm, 194 nm, 253.6 nm, 365 nm and 400 nm. In another instance, the broadband UV lamp may include, but is not limited to, a Hg—Xe lamp, a Xe lamp, a Kr lamp, an Argon lamp or combinations thereof. In another instance, lamp source may be laser produced or laser sustain plasma source. It is further noted herein that the spectra emitted by a given broadband lamp may be tuned by the implemented gas type or pressure of the lamp. In some embodiments, the broadband lamp suitable for emitting ultraviolet light may include, but is not limited to, a DC lamp, a pulsed AC lamp, an RF lamp, a laser-sustained lamp, a laser-produced plasma (LPP) based lamp or combinations thereof.

In one embodiment, oxygen gas ($O_2$) can be injected in the chamber. In another embodiment, $H_2O$ (water, steam) can be injected in the chamber. Notably, the DUV light can dissociate $H_2O$ or $O_2$, thereby facilitating step 402. In step 402, the silicon film reacts with the oxygen, thereby growing a silicon oxide. In step 403, fluorine can be diffused in the chamber during the silicon oxide formation. In one embodiment, a fluorine gas $F_2$ can be diffused in the chamber. In another embodiment, atomic fluorine (F) (provided by disassociated $F_2$ or another precursor) can be diffused instead of fluorine gas. As a result of the diffusion, in step 404, a 1-10 nm thick fluorine-doped silicon oxide film can be formed. In one embodiment, this thickness can be achieved within 0.5 to 3 hours based on the wavelength of the DUV light in step 401, the reaction time in step 402, and the amount of fluorine diffused in step 403. In one embodiment, the silicon film can be formed directly on a boron (B) film, which can provide additional protection against radiation.

In one embodiment, a wet-chemical technique called "sol-gel" can be used as a precursor to silicon oxide. An exemplary technique begins with a colloidal solution (sol) that acts as the precursor for an integrated network (or gel) of either discrete particles or network polymers. Sol gel can be easily doped with other materials. Exemplary deposition methods for sol gel are described in "Review on Sol-Gel Derived Coatings: Process, Techniques and Optical Applications", by S. M. Attia et al., J. Mater. Sci. Techno, Vol. 18, No. 3, 2002, "Energy and Technology Review", LLNL, October 1985, and "Deposition of Doped TiO2 Thin Film by Sol Gel Technique and its Characterization: A Review", by A. M Gaur et al., Proceedings of the World Congress on Engineering 2011, Vol II WCE 2011, Jul. 6-8, 2011, London, U.K. In general, the sol gel technique follows the basic process below:

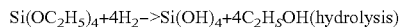
$Si(OC_2H_5)_4 + 4H_2 \rightarrow Si(OH)_4 + 4C_2H_5OH$ (hydrolysis)

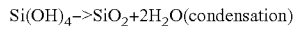
$Si(OH)_4 \rightarrow SiO_2 + 2H_2O$ (condensation)

Overall Reaction:

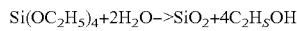
$Si(OC_2H_5)_4 + 2H_2O \rightarrow SiO_2 + 4C_2H_5OH$

Note that the preparation of thin films by spin coating of sol precursor is preferred to other sol-gel variants because of its compatibility with current practices of silicon technology. Note further that optical and/or electrical properties of the sol gel can be enhanced by chemical or nanoparticle doping. In addition, the structure and morphology of the sol gel can be changed by increasing of the annealing temperature.

Figure 5:
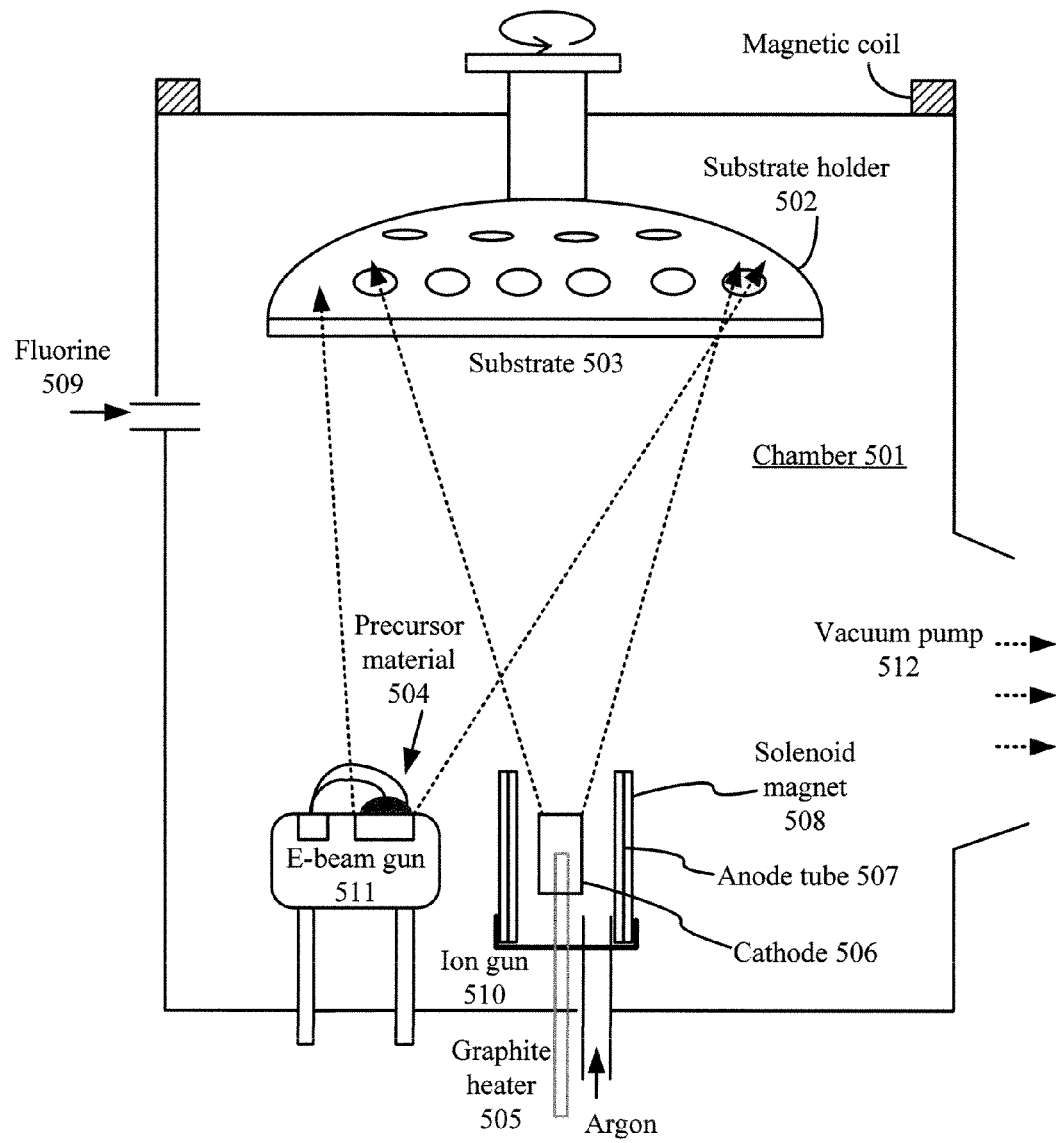
FIG. 5 illustrates an exemplary ion-beam assisted deposition system that can be used to form a fluorine-doped silicon oxide film.

FIG. 5 illustrates an exemplary ion-beam assisted deposition system that can be used to form a fluorine-doped silicon oxide film. This system includes a chamber 501 in which a substrate holder 502 can rotate a substrate 503 during deposition. In one preferred embodiment, substrate 503 is a silicon substrate. An e-beam gun 511 is used to melt and evaporate a precursor material 504. An exemplary precursor material 504 in one embodiment could be silicon oxide, silica, silicon, silane, or siloxane. An ion gun 510 includes a cathode 506, an anode tube 507, and solenoid magnet 508. Ion gun 510 provides a positive voltage to anode tube 507 and a negative voltage to cathode 506. A graphite heater 505 within cathode 506 is heated to facilitate cathode 506 emitting electrons. These electrons allow an inert gas (e.g. argon) to be ionized and form plasma. A solenoid magnet 508 helps focus the electrons to enhance the plasma production. The ions from the plasma are repelled by the anode electric field to create the ion beam. In this configuration, ion gun 510 can generate a beam of ions with a well-defined energy distribution. The beam of ions from ion gun 510 can give up electrons to provide energy to the evaporative material from e-beam gun 511, thereby facilitating the oxide film growth on substrate 503. Fluorine 509 can be diffused into chamber 501 during the silicon oxide formation. In one embodiment, a fluorine gas $F_2$ can be diffused in the chamber. In another embodiment, atomic fluorine (F) (provided by disassociated $F_2$ or another precursor) can be diffused instead of fluorine gas. A vacuum pump 512 can be controlled to expel the plasma, evaporative material, and the fluorine, as necessary in the processing. As a result of the diffusion, a 1-10 nm thick fluorine-doped silicon oxide film can be formed. In one embodiment, this thickness can be achieved within 0.5 to 3 hours based on the energy of the plasma, the amount of evaporative material output by the e-beam gun, and the amount of fluorine diffused. Ion-assisted deposition can advantageously vary the plasma energy to suit process requirements, provide a pin-hole-free surface of the fluorine-doped silicon oxide, and provide enhanced damage resistance and stability over time.

Figure 6:
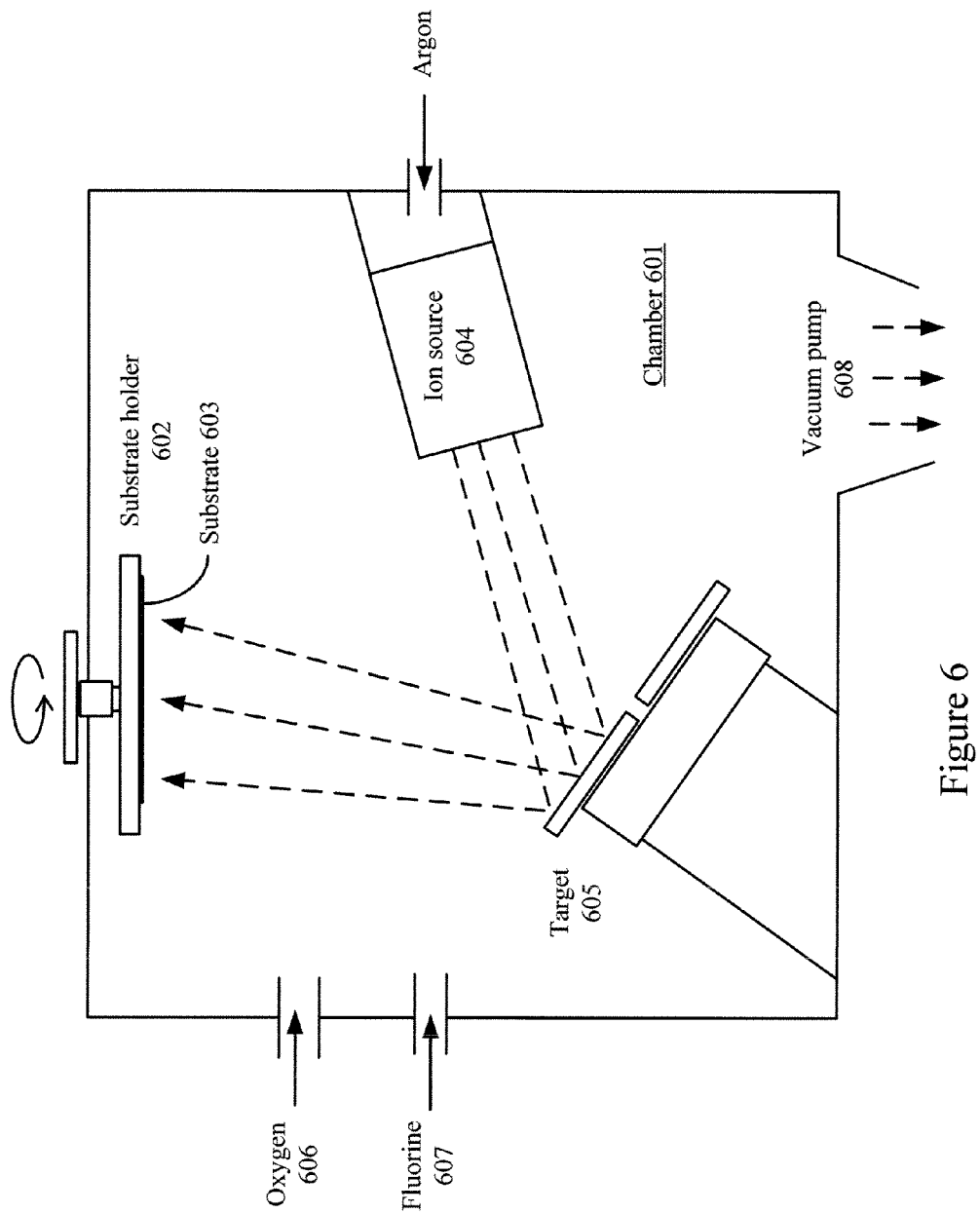
FIG. 6 illustrates an exemplary ion-beam sputtering deposition system that can be used to form a fluorine-doped silicon oxide film.

FIG. 6 illustrates an exemplary ion-beam sputtering deposition system that can be used to form a fluorine-doped silicon oxide film. This system includes a chamber 601 in which a substrate holder 602 can rotate a substrate 603 during deposition. In one preferred embodiment, substrate 603 is a silicon substrate. An ion source 604 bombards a target 605 with high energy atoms (e.g. from an inert gas, such as argon). In one embodiment, the energy can exceed 1000 eV. Target 605 can include silicon oxides, silica, silicon, silanes, or siloxanes. Both oxygen 606 and fluorine 607 can be diffused into chamber 601, wherein in the presence of the deflected high-energy atoms, a fluorine-doped silicon oxide is formed on substrate 603. A vacuum pump 608 can be used to expel oxygen 606 and/or fluorine 607 as necessary in the diffusion process. In one embodiment, this thickness can be achieved within 0.5 to 3 hours based on the energy of the atoms from ion source 604, the amount of oxygen diffused, and the amount of fluorine diffused. Ion beam sputtering can provide a very robust coating with excellent thickness control for thin layers. Ion beam sputtering also ensures a coating with low absorption and scatter, low surface roughness, and minimal wavelength shift.

Figure 7:
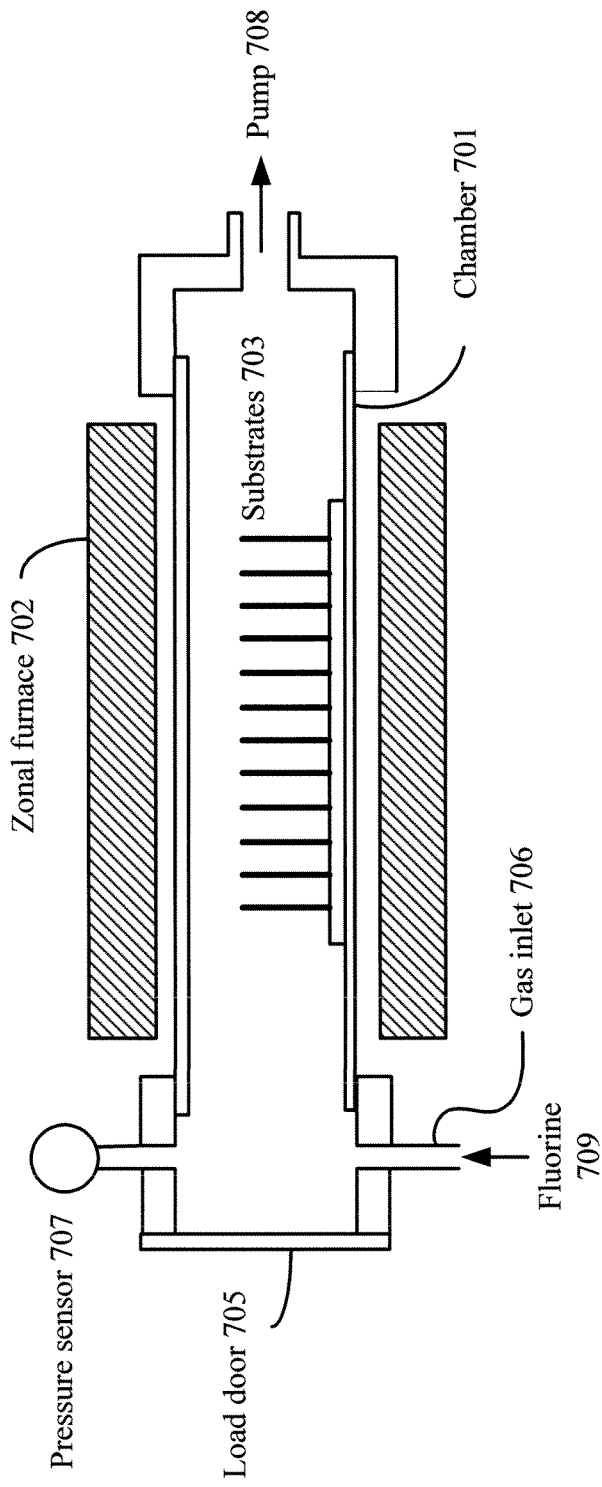
FIG. 7 illustrates an exemplary chemical vapor deposition (CVD) system that can be used to form a fluorine-doped silicon oxide film.

FIG. 7 illustrates an exemplary chemical vapor deposition (CVD) system that can be used to form a fluorine-doped silicon oxide film. This CVD system includes a chamber 601 into which a plurality of substrates 703 can be loaded via a load door 705. In one embodiment, chemical reactions can be initiated by an operating pressure controlled by a pressure sensor 707. Typical depositions can be performed using either low-pressure CVD (e.g. below atmospheric pressure, but above $10^{-8}$ torr) or ultra-high vacuum CVD (e.g. below $10^{-8}$ torr). In one embodiment, a zonal furnace 702 can be used to rapidly heat substrates 703 to minimize unwanted gas-phase reactions that can result in particle formation. A gas inlet 706 can be used to inject source gases including fluorine 709, silane ($SiH_4$) 710, and oxygen 711. In this deposition process, substrates 703 are exposed to the source gases under a predetermined pressure, and in some embodiments a predetermined heating, which causes a chemical decomposition and reaction to generate the fluorine-doped silicon oxide film.

Other exemplary methods for forming fluorine-doped silicon oxide film include, but are not limited to, plasma deposition, plasma enhanced CVD, magnetron coatings, electron beam evaporation (e-beam), and thermal evaporation.

Optimization of a fluorine-doped silicon oxide film for optical performance, radiation damage resistance and protection, environmental robustness, and minimal contamination buildup can be done by tuning the thickness, density, and stoichiometry (i.e. the relative quantities of reactants and products in chemical reactions) of the film and its fabrication. For example, varying the thickness of a silicon oxide thin film capping layer can change the characteristics of carbon buildup on a molybdenum (Mo)/silicon (Si) multilayer mirror (MLM) optic. In at least one study, described in "Controlling Contamination in Mo/Si Multilayer Mirrors by Si Surface-capping Modifications", M. Malinowski, et al, Proceedings of SPIE Vol. 4688 (2002), it was shown that a 3 nm silicon-capped Mo/Si MLM had the highest as-received reflectivity, but also maintained that reflectivity the longest under EUV and hydrocarbon vapor pressure exposure (samples studied were those with silicon capping layers ranging from 2 nm to 7 nm). The results from this study are consistent with a standing wave electric field near the surface; however, its presence may also result in undesirable carbon contamination of the MLM optic. As described below, the thickness of the fluorine-doped silicon oxide film can be designed to minimize the near-surface electric field, thereby reducing carbon buildup. But the optimal thickness must be weighed in with optical performance for specific optic applications.

A standing wave electric field near the surface of the optical element may depend on the material under the thin protective film. Therefore, the selection of such underlying layers should be considered. For example, FIG. 8 (submitted in "Controlling Contamination in Mo/Si Multilayer Minors by Si Surface-capping Modifications", M. Malinowski, et al, Proceedings of SPIE Vol. 4688 (2002)) is a graph plotting electric field intensity versus a depth relative to a thin $SiO_2$ film surface for an MLM optic. In this case, the MLM optic is a Mo/Si multilayer typical of EUV mirrors. As shown, the electric field intensity changes significantly based on the thickness of the thin film. It is posited that similar intensity changes may occur based on the ratio of Mo/Si, the density of the thin film, and the doping of the thin film. Therefore, in the case of using a fluorine-doped silicon oxide film, the characteristics of its underlying layers (e.g. boron, silicon nitride, silicon) may also be taken into account in some embodiments.

It is well known in the industry that the laser damage fluence of films depends on the standing-wave electric field pattern. Therefore, strategies for maximizing optics lifetime should (1) maximize the damage and environmental resistance (chemical, $H_2O$ ion erosions, etc.) of optical coatings and (2) minimize both the defective nature of the coating and the electric field intensity at critical points. With respect to the defective nature of the coating, note that coating technology needs to avoid incipient inclusions, voids, grooves, submicroscopic cracks, and pores at surfaces or interfaces in optical coatings or films because these can lead to local enhancement of the electric field strength in radiation beams. Thus, during surface and coating preparation, voids, pores, bubbles, inclusions, and deposition of additional absorbing inclusions should be avoided.

Figure 8:
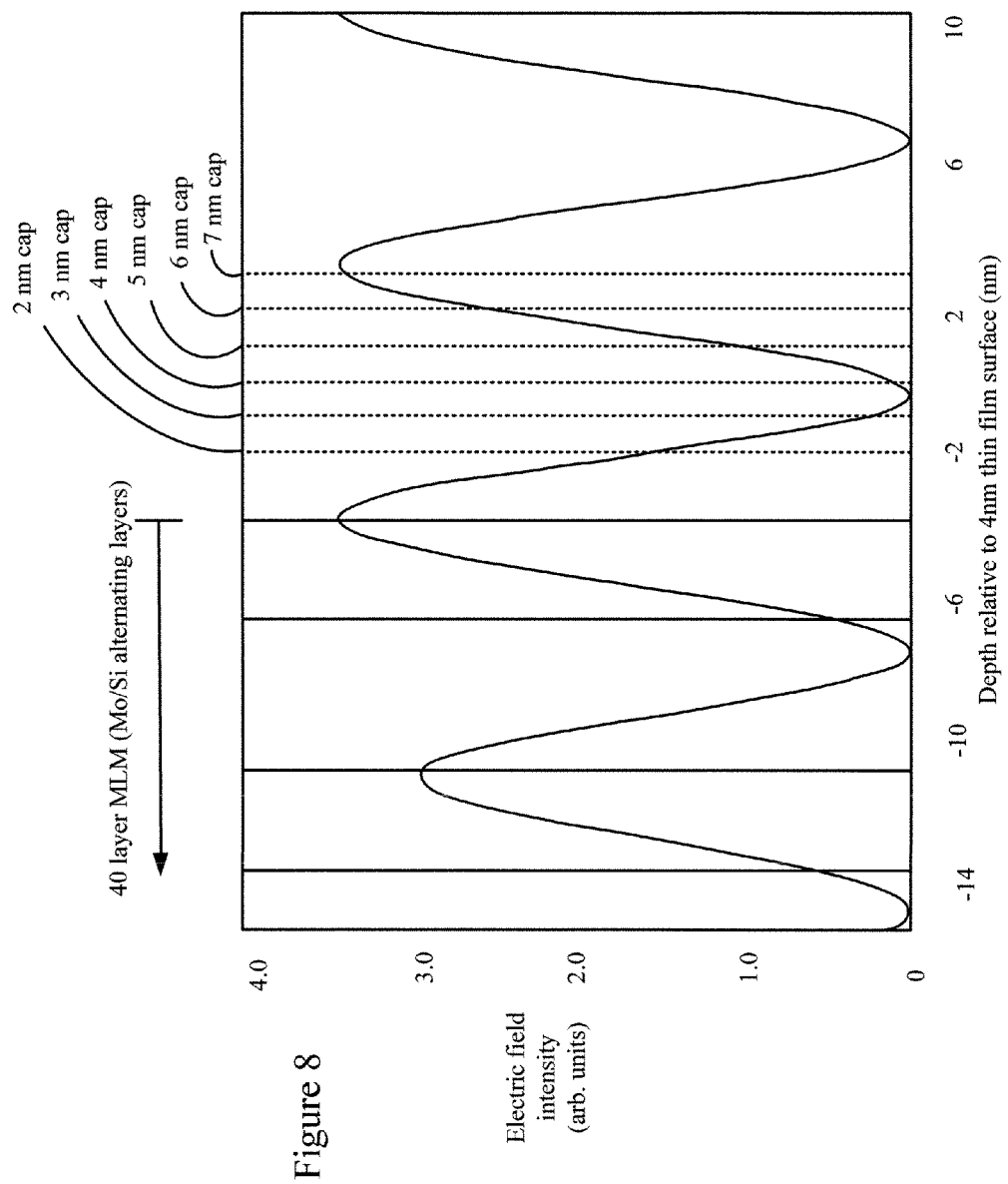
FIG. 8 is a graph plotting electric field intensity versus a depth relative to a thin $SiO_2$ film surface for a multi-layer mirror optic.

As shown in FIG. 8, the interference between the electromagnetic wave flowing in the forward direction (depths 0 to 10) inside the film and the waves reflected at the interfaces flowing in the backward direction (depths 0 to −14) result in the formation of a standing wave electric field pattern (see FIG. 8 above). As described in further detail below, the amount of energy absorbed by the film is determined by the intensity of light, which turns out to be proportional to the square of the electric field magnitude. Thus, the minimization of the local electric field intensity inside the coating allows obtaining higher damage threshold fluences. A good control on the electric field intensity can be obtained by a proper choice of the parameters involved in the coating design, i.e. refractive index, density, stoichiometry, and thickness of the thin film.

The energy absorbed per unit volume (e(z)) in a weakly absorbing medium with refractive index n(z) and an absorption coefficient a(z) is given by:

$$e(z) = \alpha(z) n(z) [E_z/E_o]^2 F$$

where F is the incident laser fluence (J/cm²), and $|(E_z/E_o)|^2$ is the electric field intensity normalized to the incident electric field intensity value. This computation is described in further detail in P. A. Temple, Appy. Phys Lett. 34, page 677, (1979).

The fluorine-dope silicon oxide film described above may be included in any one of a plurality of optical components, which in turn can be placed in mask, reticle, and wafer inspection systems for increased performance.

Figure 9:
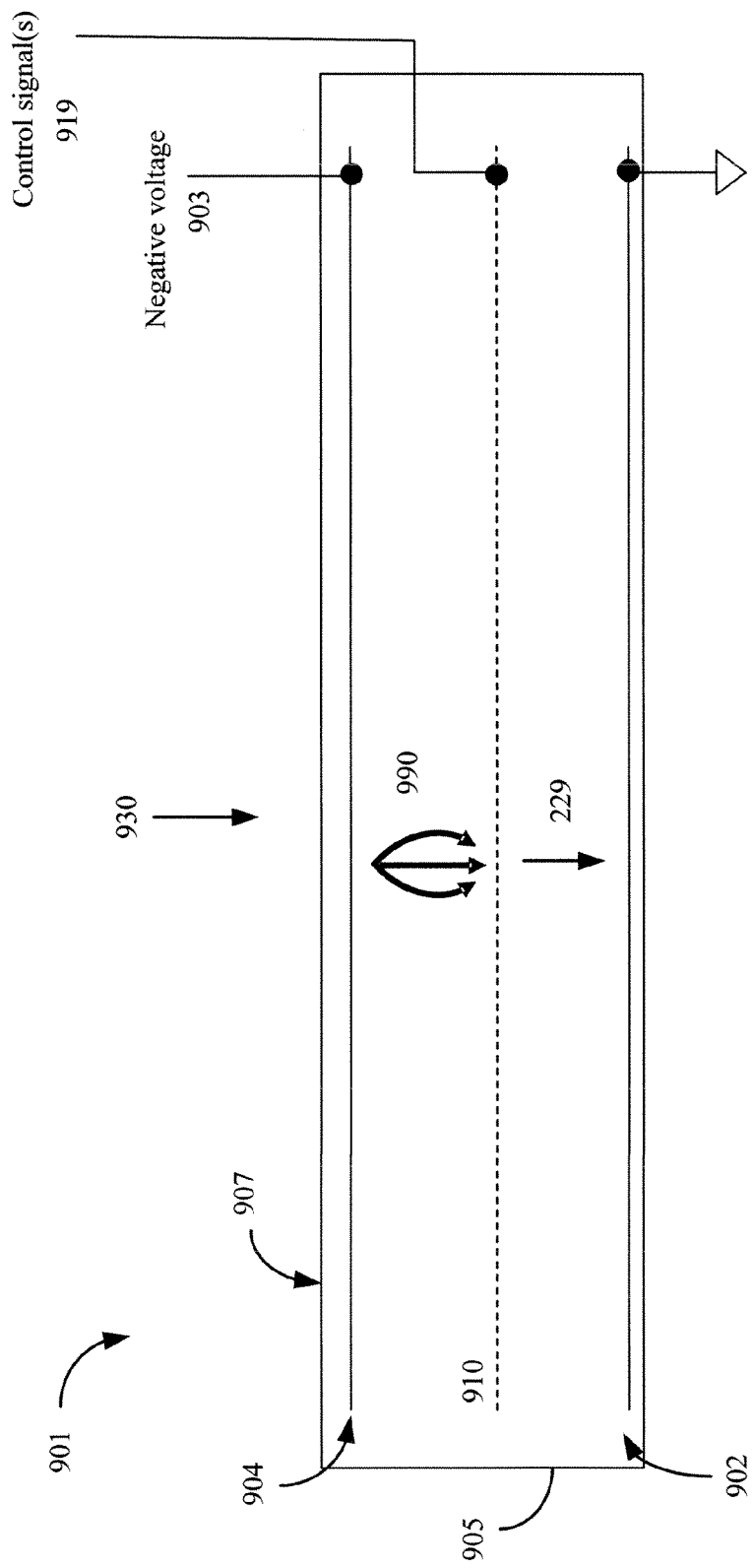
FIG. 9 illustrates an electron beam charge-coupled device (EBCCD).

For example, FIG. 9 illustrates an electron beam charge-coupled device (EBCCD) 901 including a sealed tube 905 that encloses a light-sensitive photocathode 904 and a CCD 902 in a vacuum environment. A top surface of tube 905 comprises a window 907 that is transparent at the wavelengths of interest. For UV sensitive EBCCD detectors, this window preferably comprises a very pure grade of quartz, fused silica, or alumina (sapphire). In one embodiment, the outside surface of window 907 is coated with the above-described fluorine-doped silicon oxide.

Photocathode 904 is positioned immediately adjacent to window 907 or may be implemented as a coating of window 907. The photocathode material may be substantially similar to any photocathode material known in the art for use in photomultiplier, image intensifier, or CCD detectors. In preferred embodiments, photocathode 904 may comprise one or more alkali metals such as Cesium, or may comprise a semiconductor such gallium nitride (GaN) or gallium arsenide (GaAs). Photocathode 904 is held at a negative voltage 903 relative to CCD 902. In some embodiments, negative voltage 903 may be approximately 1000 V. In other embodiments, negative voltage 903 may be a few hundred volts or several tens of volts.

CCD 902, which is positioned near a bottom surface of tube 905, is a thinned CCD oriented so that the electrons impinge first on its back surface (i.e. a back-thinned CCD). A back-thinned COD is typically formed by forming transistors and other devices on a surface of a silicon substrate of, for example, approximately 500 µm thick. Doping can be used for creating both p-type and n-type devices. Because these devices are formed from a variety of materials of different thicknesses, some of the electrons reaching the CCD may be blocked or absorbed by these devices as well as by the thick silicon. Therefore, a significant portion of the silicon is removed to ensure that as many of the electrons as possible can be detected when the electrons impinge on the back surface. In standard embodiments, the thickness of the resulting silicon is on the order of 25 µm. In one embodiment, the top surface of CCD 902 is coated with the above-described fluorine-doped silicon oxide.

Figure 10:
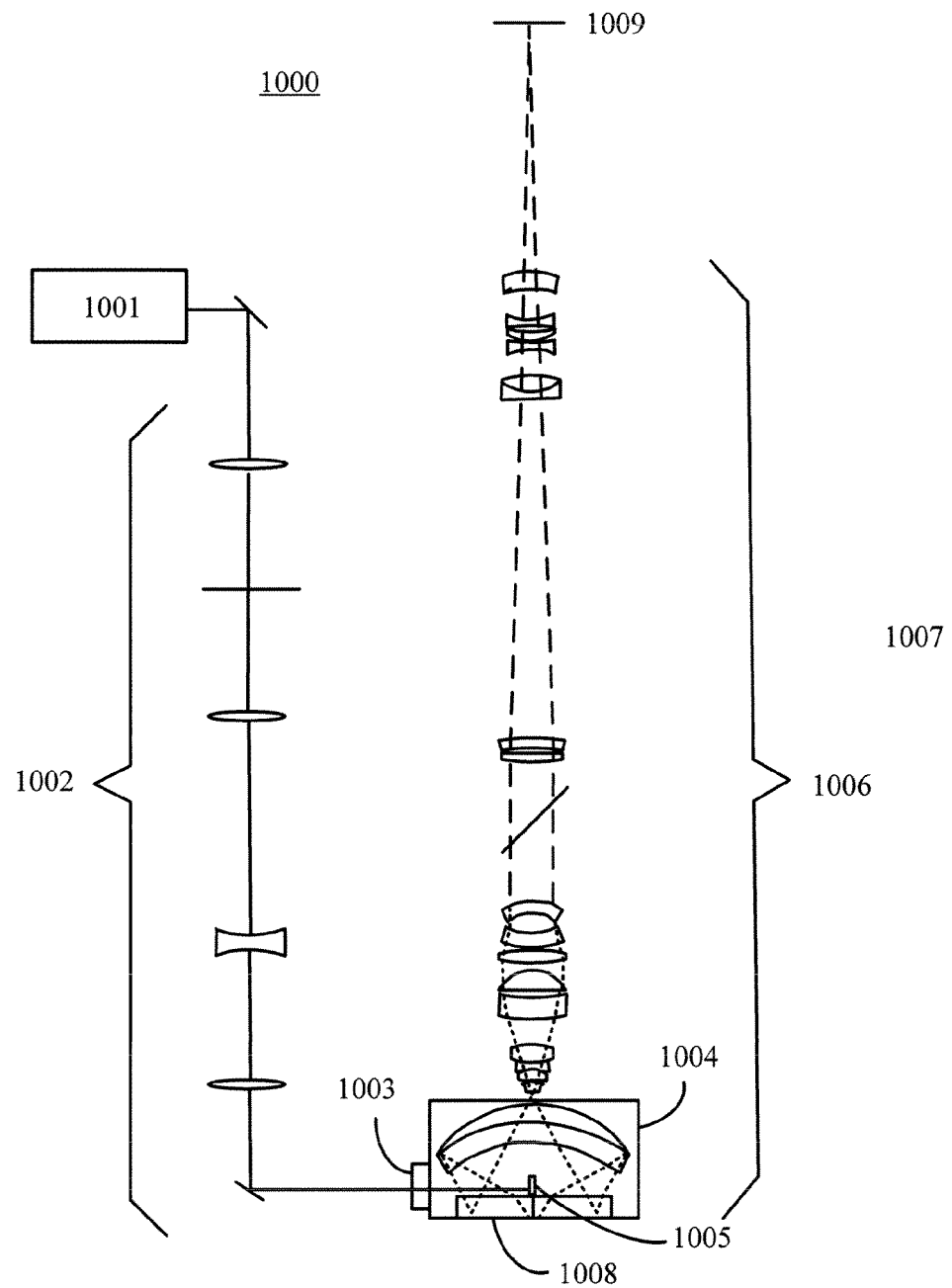
FIG. 10 illustrates an exemplary dark-field catadioptric imaging system.

FIG. 10 illustrates an exemplary dark-field catadioptric imaging system 1000 including a laser 1001, adaptation optics 1002 to control the illumination beam size and profile on the surface being inspected, an aperture and window 1003 in a mechanical housing 1004, and a prism 1005 to redirect light from the laser along the optical axis at normal incidence to the surface of a sample 1008. Prism 1005 also directs the specular reflection from surface features of sample 1008 and reflections from the optical surfaces of an objective lens 1006 along the optical path to an image plane (or detector) array 1009. Lenses for objective lens 1006 can be provided in the general form of a catadioptric objective, a focusing lens group, and a zooming tube lens section. In a preferred embodiment, because the dark-field scattered signal can be weak, image plane (or detector) array 1009 can be advantageously implemented by an EBCCD detector having a fluorine-doped silicon oxide layer (either on its window or on its sensor). The EBCCD having the above-described control device is well suited to this application because of its high spatial resolution and, in some embodiments, because of the possibility of controlling its gain in response to, or anticipation of, changes in the scattered light level depending on patterns on the wafer being inspected. In one embodiment, the outside surface of window 1003 and/or at least one optical component of adaptation optics 1002 and objective lens 1006 includes the above-described fluorine-doped silicon oxide film. Published Patent Application 2007/0002465, which published on Jan. 4, 2007 and is incorporated by reference herein, describes certain aspects of system 1000 in further detail.

Figure 11A:
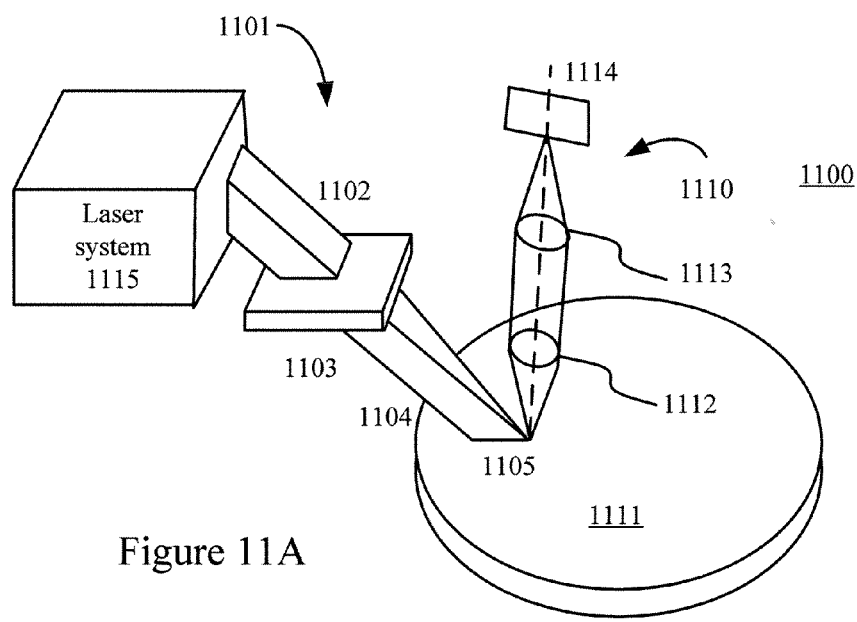
FIG. 11A illustrates an exemplary surface inspection apparatus.

FIG. 11A illustrates a surface inspection apparatus 1100 that includes an illumination system 1101 and a collection system 1110 for inspecting areas of a surface 1111. As shown in FIG. 11A, a laser system 1115 is configured to direct a light beam 1102 through a lens 1103. Lens 1103 is oriented so that its principal plane is substantially parallel to surface 1111 and, as a result, illumination line 1105 is formed on surface 1111 in the focal plane of lens 1103. In addition, light beam 1102 and focused beam 1104 are directed at a non-orthogonal angle of incidence to surface 1111. In particular, light beam 1102 and focused beam 1104 may be directed at an angle between about 1 degree and about 85 degrees from a normal direction to surface 611. In this manner, illumination line 1105 is substantially in the plane of incidence of focused beam 1104. In some embodiments, illumination line might be approximately 1 or 2, or a few, mm long and 1, 2 or a few μm wide. In some embodiments, instead of a line focus, the illumination may be focused into a series of discrete spots.

Collection system 1110 includes a lens 1112 for collecting light scattered from illumination line 1105 and a lens 1113 for focusing the light coming out of lens 1112 onto a device, such as a detector 1114. Dynamic adjustment of the gain of detector 1114 is important in this kind of inspection system because the scattered and diffracted light levels (and the efficiency of the filters) can vary dramatically from one region of a wafer to another due to the different patterns on the wafer. In one embodiment, at least one optical component of detector 1114, collection system 1110, and illumination system 1101 includes the above-described fluorine-doped silicon oxide film.

Figure 11B:
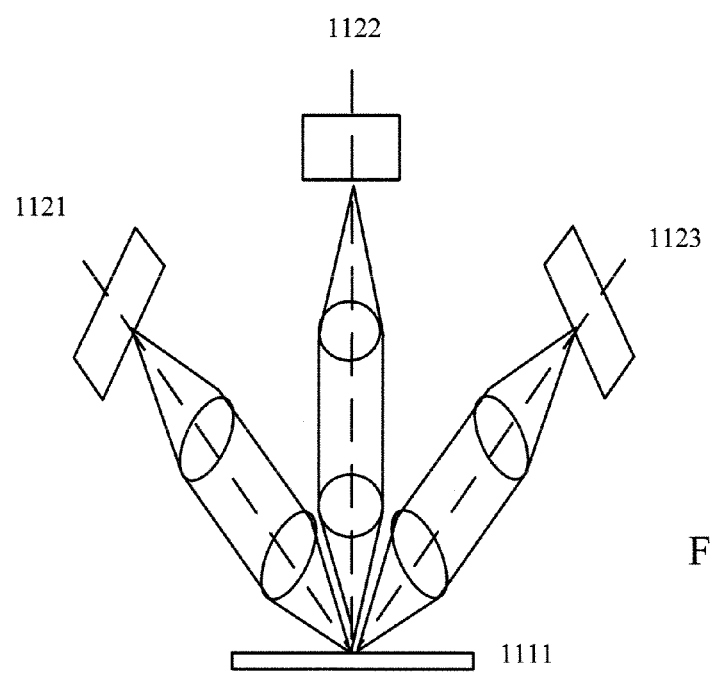
FIG. 11B illustrates an exemplary array of collection systems for a surface inspection apparatus.

In one embodiment, detector 1114 may include a linear array of detectors. In such cases, the linear array of detectors within detector 1114 can be oriented parallel to illumination line 1115. In one embodiment, multiple collection systems can be included, wherein each of the collection systems includes similar components, but differ in orientation. For example, FIG. 11B illustrates an exemplary array of collection systems 1121, 1122, and 1123 for a surface inspection apparatus (wherein its illumination system, e.g. similar to that of illumination system 1101, is not shown for simplicity). U.S. Pat. No. 7,525,649, which issued on Apr. 8, 2009 and is incorporated by reference herein, describes certain aspects of inspection system 1101 in greater detail.

Figure 12:
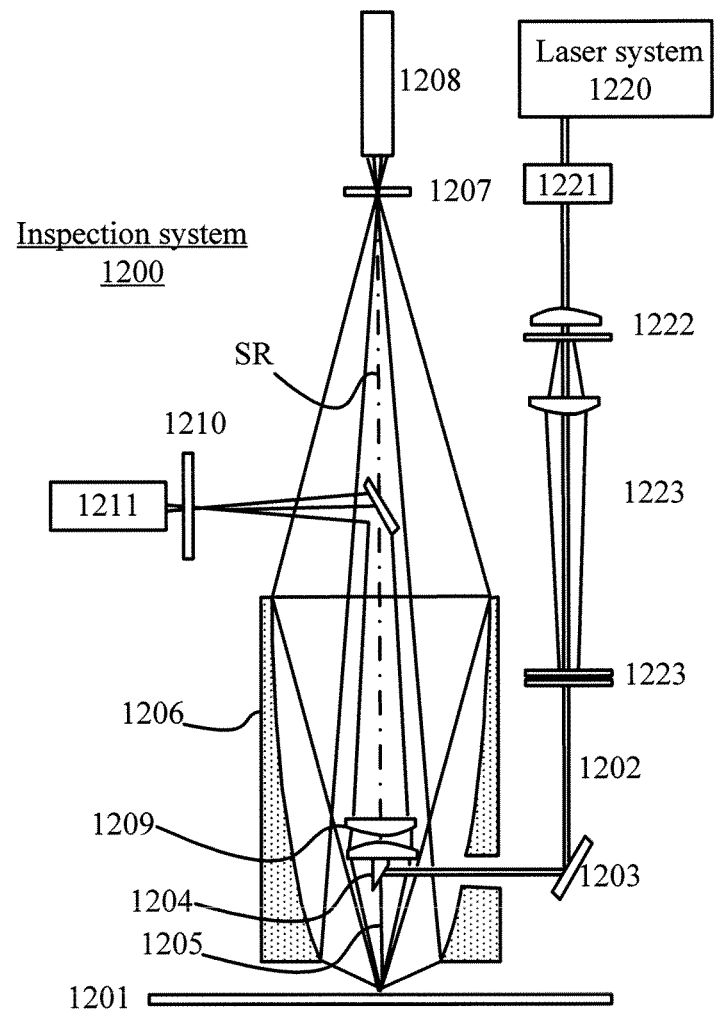
FIG. 12 illustrates a surface inspection system that can be used for inspecting anomalies on a surface.

FIG. 12 illustrates a surface inspection system 1200 that can be used for inspecting anomalies on a surface 1201. In this embodiment, surface 1201 can be illuminated by a substantially stationary illumination device portion of system 1200 comprising a laser beam generated by laser system 1220. The output of laser system 1220 can be consecutively passed through polarizing optics 1221, a beam expander and aperture 1222, and beam-forming optics 1223 to expand and focus the beam.

The focused laser beam 1202 is then reflected by a beam folding component 1203 and a beam deflector 1204 to direct the beam 1205 towards surface 1201 for illuminating the surface. In the preferred embodiment, beam 1205 is substantially normal or perpendicular to surface 1201, although in other embodiments beam 1205 may be at an oblique angle to surface 1201.

In one embodiment, beam 1205 is substantially perpendicular or normal to surface 1201 and beam deflector 1204 reflects the specular reflection of the beam from surface 1201 towards beam turning component 1203, thereby acting as a shield to prevent the specular reflection from reaching the detectors. The direction of the specular reflection is along line SR, which is normal to surface 1201. In one embodiment where beam 1205 is normal to surface 1201, this line SR coincides with the direction of illuminating beam 1205, where this common reference line or direction is referred to herein as the axis of inspection system 1200. Where beam 1205 is at an oblique angle to surface 1201, the direction of specular reflection SR would not coincide with the incoming direction of beam 1205; in such instance, the line SR indicating the direction of the surface normal is referred to as the principal axis of the collection portion of inspection system 1200.

Light scattered by small particles are collected by mirror 1206 and directed towards aperture 1207 and detector 1208. Light scattered by large particles are collected by lenses 1209 and directed towards aperture 1210 and detector 1211. Note that some large particles will scatter light that is also collected and directed to detector 1208, and similarly some small particles will scatter light that is also collected and directed to detector 1211, but such light is of relatively low intensity compared to the intensity of scattered light the respective detector is designed to detect. In one embodiment, inspection system can be configured for use in detecting defects on unpatterned wafers. In one embodiment, one or more of detectors 1208 and 1211 can be implemented by an EBCCD. In one embodiment, at least one of detectors 1208 and 1211 or any other component of inspection system 1200 can include the above-described fluorine-doped silicon oxide film. U.S. Pat. No. 6,271,916, which issued on Aug. 7, 2001 and is incorporated by reference herein, describes certain aspects of inspection system 700 in greater detail.

Figure 13:
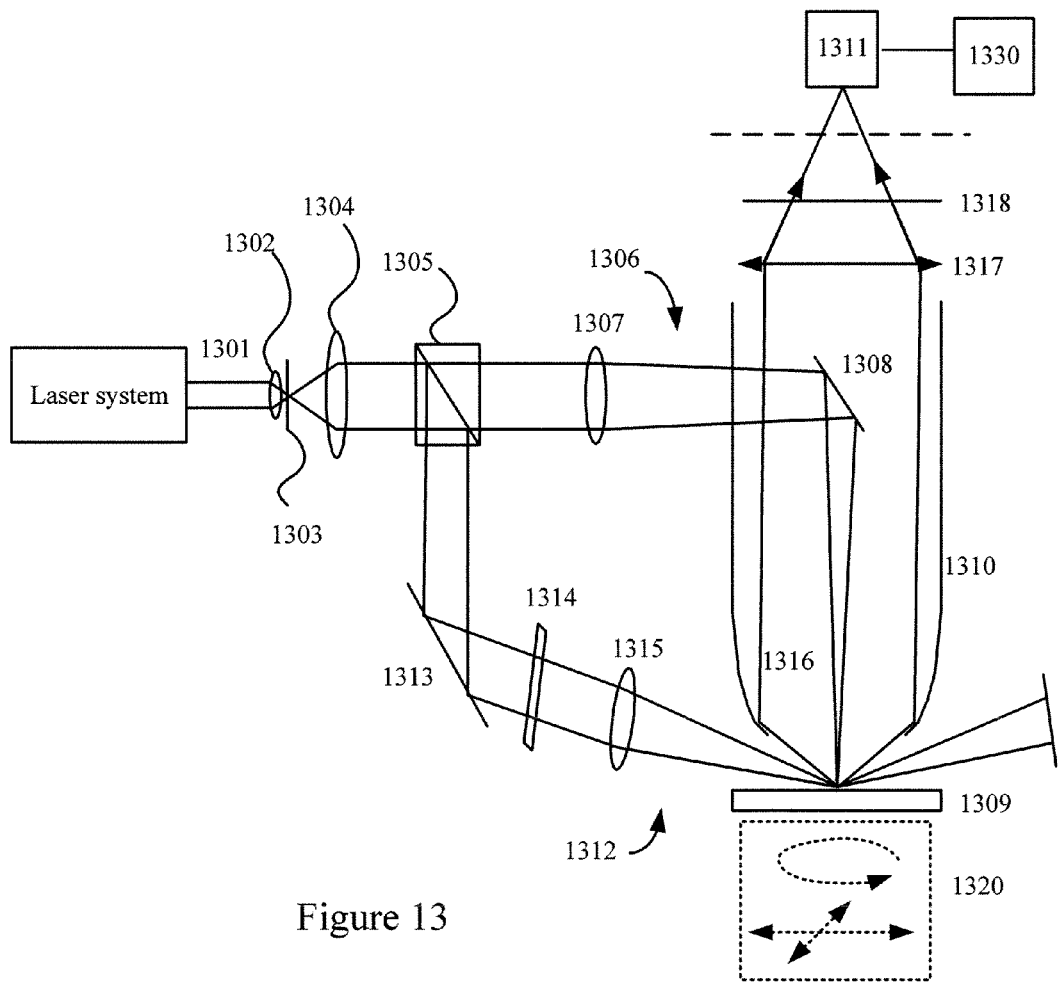
FIG. 13 illustrates a dark-field inspection system for anomaly detection using both normal and oblique illumination beams.

FIG. 13 illustrates a dark-field inspection system 1300 for anomaly detection using both normal and oblique illumination beams. In this configuration, a laser system can provide a laser beam 1301. A lens 1302 focuses the beam 801 through a spatial filter 1303 and lens 1304 collimates the beam and conveys it to a polarizing beam splitter 1305. Beam splitter 1305 passes a first polarized component to the normal illumination channel and a second polarized component to the oblique illumination channel, where the first and second components are orthogonal. In the normal illumination channel 806, the first polarized component is focused by optics 1307 and reflected by mirror 1308 towards a surface of a sample 1309. The radiation scattered by sample 1309 is collected and focused by a paraboloidal mirror 1310 to a detector 1311.

In the oblique illumination channel 1312, the second polarized component is reflected by beam splitter 1305 to a mirror 1313 which reflects such beam through a half-wave plate 1314 and focused by optics 1315 to sample 1309. Radiation originating from the oblique illumination beam in the oblique channel 1312 and scattered by sample 1309 is collected by paraboloidal mirror 1310 and focused to detector 1311. In one embodiment, detector 1311 is an EBCCD detector as described with respect to FIG. 9. The detector and the illuminated spot (from the normal and oblique illumination channels on surface 1309) are preferably at the foci of the paraboloidal mirror 1310.

Paraboloidal mirror 1310 collimates the scattered radiation from sample 1309 into a collimated beam 1316. Collimated beam 1316 is then focused by an objective 1317 and through an analyzer 1318 to detector 1311. Note that curved mirrored surfaces having shapes other than paraboloidal shapes may also be used. In one embodiment, at least one optical component of the first optics of the normal illumination channel, the second optics of the oblique illumination channel, detector 1311, and the collection optics includes a fluorine-doped silicon oxide film. An instrument 1320 can provide relative motion between the beams and sample 1309 so that spots are scanned across the surface of sample 1309. In one embodiment, computer 1330 can receive outputs of detector 1311. U.S. Pat. No. 6,201,601, which issued on Mar. 13, 2001 and is incorporated by reference herein, describes certain aspects of inspection system 1300.

Figure 14:
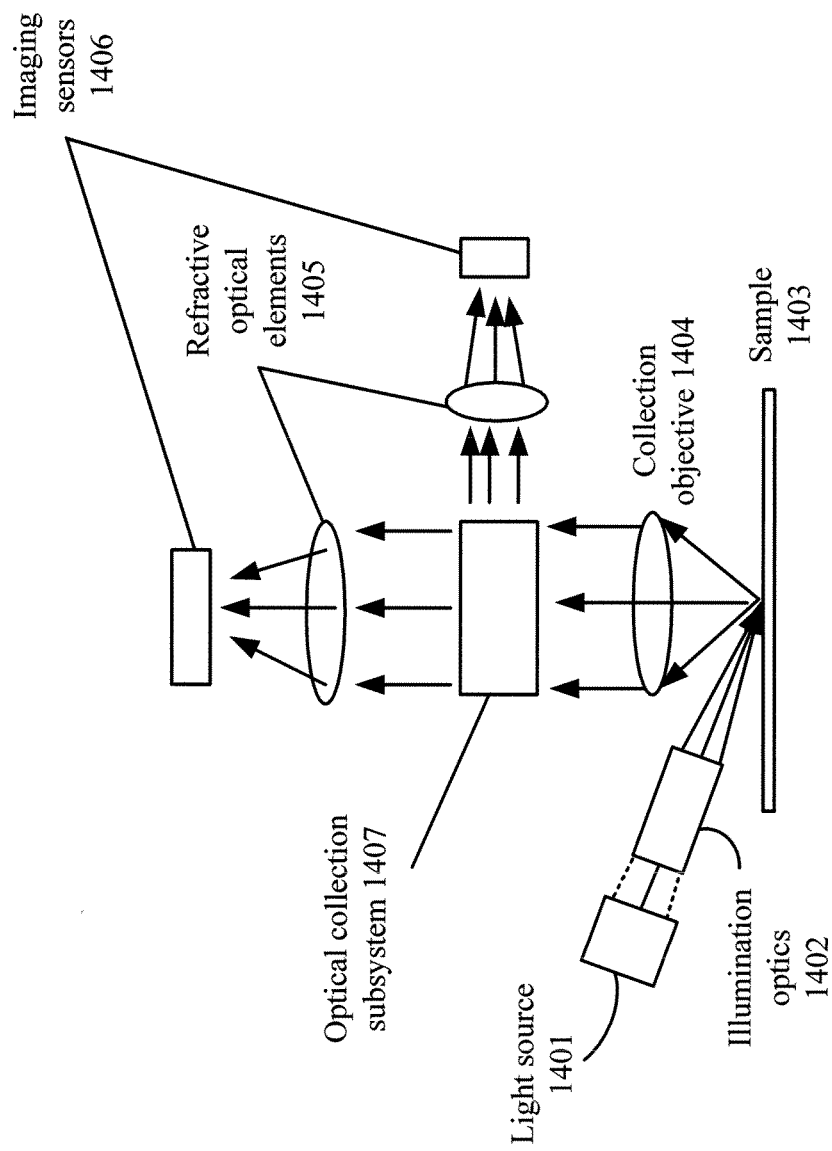
FIG. 14 illustrates a dark-field wafer inspection system.

FIG. 14 illustrates a dark-field wafer inspection system 1400. In system 1400, illumination optics 1402 receives the light beam(s) emitted by a light source 1401. In one embodiment, illumination optics 1402 may include multiple beam splitters and reflective optical elements that provide substantially parallel output light beams to a refractive optical element. That refractive optical element, in turn, can focus the multiple light beams onto a sample 1403.

An optical collection subsystem 1407 including a scattered light collector and other elements, such as one or more apertures, splitters, polarizing elements, and reflective optical elements, can direct the light scattered from sample onto two image detectors 1406. In one embodiment, optical collection subsystem 1407 may further include refractive optical elements 1405 that are configured to assist the other elements of optical collection subsystem 1407 in imaging the scattered light onto image detectors 1406. In one embodiment, at least one of image detectors 1406 can include the above-described EBCCD detector. In one embodiment, one detector may be optimized for substantially high light scattering while another detector may be optimized for substantially low light scattering. Therefore, during some portions of a scan, the optical element may be configured to direct one portion of the scattered light to one image detector optimized for substantial light scattering and to direct another, different portion of the scattered light to a different image detector that is optimized for low-light scattering. In one embodiment, at least one optical component of illumination optics 1402, optical collection subsystem 1407, and imaging sensors 1406 includes a fluorine-doped silicon oxide film. U.S. patent application Ser. No. 13/554,954, filed on Jul. 9, 2012, claiming priority from U.S. Provisional Application 61/506,892 filed on Jul. 12, 2011, describes certain aspects of system 1400 in greater detail. Both of these patent applications are incorporated by reference herein.

Figure 15:
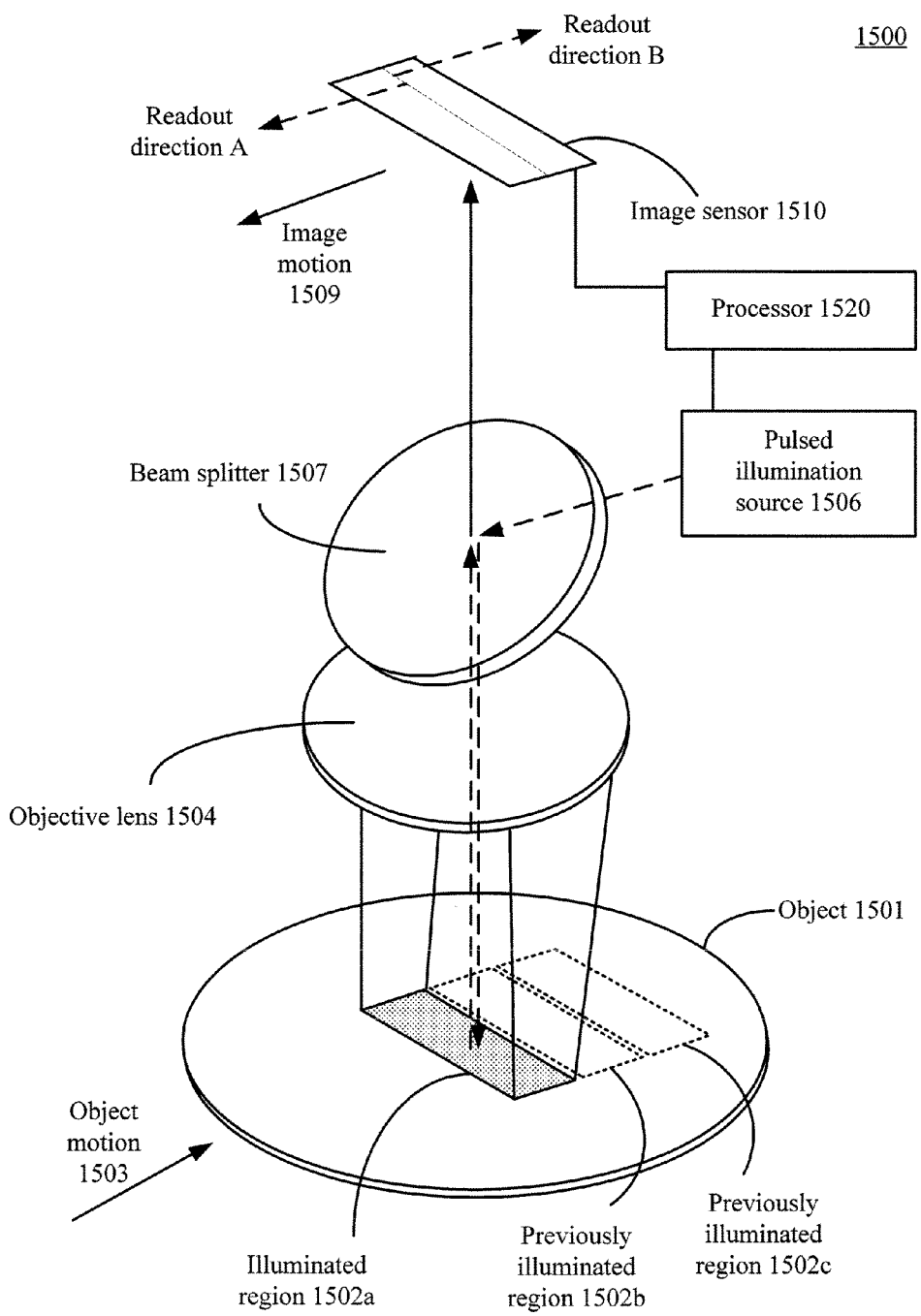
FIG. 15 illustrates an exemplary inspection/metrology system using a pulsed illumination source with a continuously moving object, such as a wafer, mask, or reticle.

FIG. 15 illustrates an exemplary inspection/metrology system 1000 using a pulsed illumination source 1506 with a continuously moving object 1501, such as a wafer, mask, or reticle. Advantageously, pulsed illumination 1506 can output a long pulse. Exemplary sources for pulsed illumination 1506 can include a Q-switched laser or a pulsed lamp. A Q-switched laser uses a variable attenuator inside the laser's optical resonator to produce light pulses with extremely high peak power. These light pulses are much higher power than those produced by the same laser operating in continuous mode. A pulsed lamp could be implemented by a deep ultraviolet (DUV) excimer or an extreme ultraviolet (EUV) source. In one preferred embodiment, the pulse duration is close to or somewhat longer than the line period of the time delay integration (TDI) performed.

In system 1500, a beam splitter 1507 would direct illumination pulses from pulsed illumination source 1506 to an objective lens 1504, which would focus that light onto object 1501. Reflected light from object 1501 would then be directed to an image sensor 1510. In one embodiment, image sensor 1510 can be implemented using the above-described EBCCD of FIG. 9. Note that other well-known optical components for directing and focusing of the light are not shown for simplicity in FIG. 15. In one embodiment, at least beam splitter 1507 or another optical component, such as image sensor 1510, includes a fluorine-doped silicon oxide film. A processor 1520, which is coupled to image sensor 1510, is configured to provide synchronization of illumination pulses from pulsed illumination source 1506 with control and data signals to and from image sensor 1510 as well as analysis of the image data. In the above-described configuration, object 1501 has an object motion 1503 and the image on the image sensor 1510 has an image motion 1509.

In accordance with one aspect of system 1500, because of object motion 1503, the illuminated region will continuously move across object 1501 as indicated by illuminated region 1502a (e.g. time period N), previously illuminated region 1502b (e.g. time period N−1), and previously illuminated region 1502c (e.g. time period N−2). Each of illuminated regions 1502a, 1502b, and 1502c can be a thin rectangular-shaped region (not shown to scale for ease of viewing). Note the regions are shown separated for clarity, but may overlap to provide 100% imaging coverage, or for additional redundancy and performance during defect detection.

In accordance with another aspect of system 1500, image sensor 1510 can perform a TDI-mode operation during an illumination pulse. During this TDI-mode operation, charges stored by pixels of the image sensor are shifted only in a first direction. System 1500 can also perform a split-readout operation during non-illumination. During this split-readout operation, first charges stored by first pixels of the image sensor are shifted in the first direction and second charges stored by second pixels of the image sensor are concurrently shifted in a second direction, the second direction being opposite to the first direction.

Thus, system 1500 can advantageously combine beneficial properties of TDI readout mode with fast readout capability of pulsed image architectures. Other aspects of system 1500 are described in further detail in U.S. Patent Application 61/735,427, entitled "Method And Apparatus For High Speed Acquisition Of Moving Images Using Pulsed Illumination", filed on Dec. 10, 2012, which is incorporated by reference herein.

Figure 16:
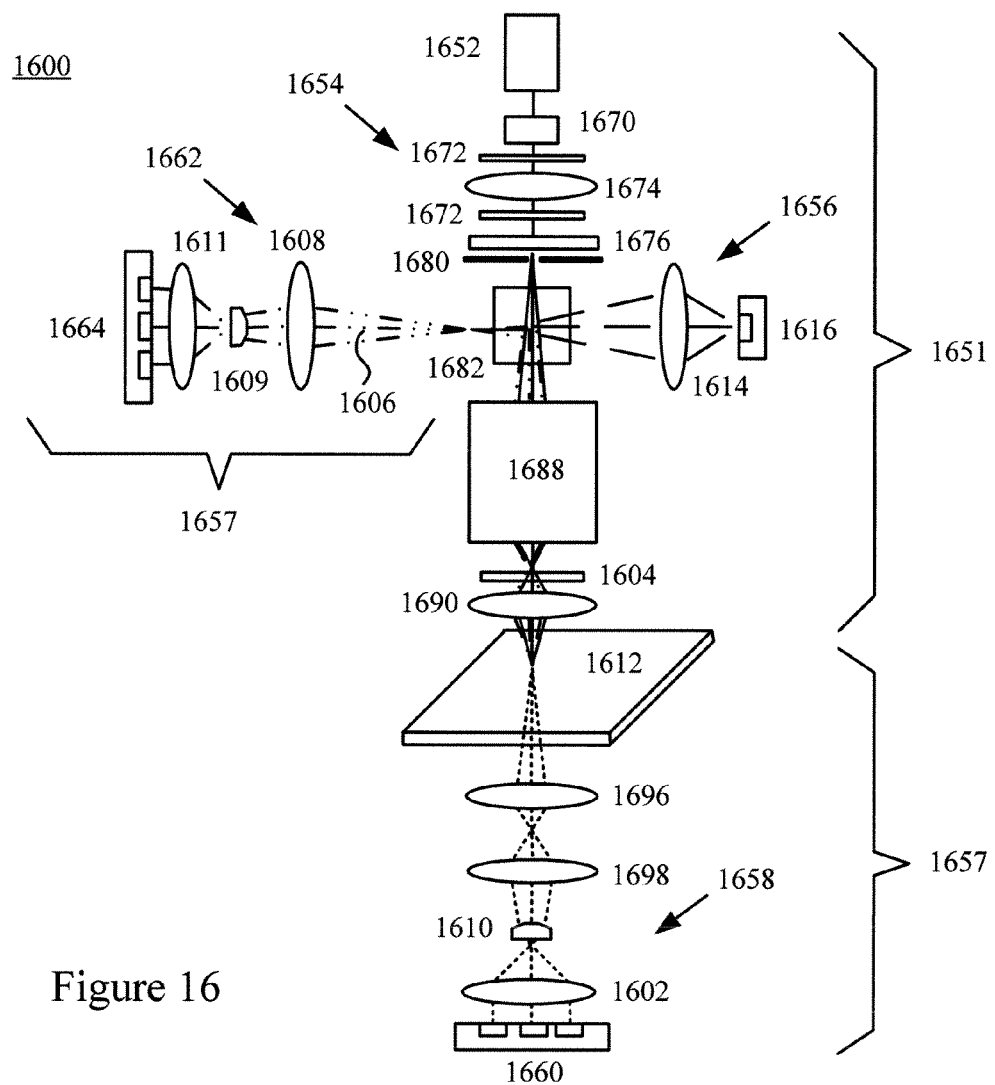
FIG. 16 illustrates an exemplary optical inspection system for inspecting the surface of a substrate.

FIG. 16 illustrates an exemplary optical inspection system 1600 for inspecting the surface of a substrate 1612. System 1600 generally includes a first optical arrangement 1651 and a second optical arrangement 1657. As shown, first optical arrangement 1651 includes at least a light source 1652, inspection optics 1654, and reference optics 1656, while the second optical arrangement 1657 includes at least transmitted light optics 1658, transmitted light detectors 1660, reflected light optics 1662, and reflected light detectors 1664. In one embodiment, at least one of transmitted light optics 1658, transmitted light detectors 1660, reflected light optics 1662, and reflected light detectors 1664 include the above-described fluorine-doped silicon oxide film.

Light source 1652 is configured to emit a light beam that passes through an acousto-optic device 1670, which is arranged for deflecting and focusing the light beam. Acousto-optic device 1670 may include a pair of acousto-optic elements, e.g. an acousto-optic pre-scanner and an acousto-optic scanner, which deflect the light beam in the Y-direction and focus it in the Z-direction. By way of example, most acousto-optic devices operate by sending an RF signal to quartz or a crystal such as $TeO_2$. This RF signal causes a sound wave to travel through the crystal. Because of the travelling sound wave, the crystal becomes asymmetric, which causes the index of refraction to change throughout the crystal. This change causes incident beams to form a focused travelling spot which is deflected in an oscillatory fashion.

When the light beam emerges from acousto-optic device 1670, it then passes through a pair of quarter wave plates 1672 and a relay lens 1674. Relay lens 1674 is arranged to collimate the light beam. The collimated light beam then continues on its path until it reaches a diffraction grating 1676. Diffraction grating 1676 is arranged for flaring out the light beam, and more particularly for separating the light beam into three distinct beams, which are spatially distinguishable from one another (i.e. spatially distinct). In most cases, the spatially distinct beams are also arranged to be equally spaced apart and have substantially equal light intensities.

Upon leaving the diffraction grating 1676, the three beams pass through an aperture 1680 and then continue until they reach a beam splitter cube 1682. Beam splitter cube 1682 (in combination with the quarter wave plates 1672) is arranged to divide the beams into two paths, i.e. one directed downward and the other directed to the right (in the configuration shown in FIG. 16). The path directed downward is used to distribute a first light portion of the beams to substrate 1612, whereas the path directed to the right is used to distribute a second light portion of the beams to reference optics 1656. In most embodiments, most of the light is distributed to substrate 1612 and a small percentage of the light is distributed to reference optics 1656, although the percentage ratios may vary according to the specific design of each optical inspection system. In one embodiment, reference optics 1656 can include a reference collection lens 1614 and a reference detector 1616. Reference collection lens 1614 is arranged to collect and direct the portion of the beams on reference detector 1616, which is arranged to measure the intensity of the light. Reference optics are generally well known in the art and for the sake of brevity will not be discussed in detail.

The three beams directed downward from beam splitter 1682 are received by a telescope 1688, which includes several lens elements that redirect and expand the light. In one embodiment, telescope 1688 is part of a telescope system that includes a plurality of telescopes rotating on a turret. For example, three telescopes may be used. The purpose of these telescopes is to vary the size of the scanning spot on the substrate and thereby allow selection of the minimum detectable defect size. More particularly, each of the telescopes generally represents a different pixel size. As such, one telescope may generate a larger spot size making the inspection faster and less sensitive (e.g., low resolution), while another telescope may generate a smaller spot size making inspection slower and more sensitive (e.g., high resolution).

From telescope 1688, the three beams pass through an objective lens 1690, which is arranged for focusing the beams onto the surface of substrate 1612. As the beams intersect the surface as three distinct spots, both reflected light beams and transmitted light beams may be generated. The transmitted light beams pass through substrate 1612, while the reflected light beams reflect off the surface. By way of example, the reflected light beams may reflect off of opaque surfaces of the substrate, and the transmitted light beams may transmit through transparent areas of the substrate. The transmitted light beams are collected by transmitted light optics 1658 and the reflected light beams are collected by reflected light optics 1662.

With regards to transmitted light optics 1658, the transmitted light beams, after passing through substrate 1612, are collected by a first transmitted lens 1696 and focused with the aid of a spherical aberration corrector lens 1698 onto a transmitted prism 1610. Prism 1610 can be configured to have a facet for each of the transmitted light beams that are arranged for repositioning and bending the transmitted light beams. In most cases, prism 1610 is used to separate the beams so that they each fall on a single detector in transmitted light detector arrangement 1660 (shown as having three distinct detectors). Accordingly, when the beams leave prism 1610, they pass through a second transmitted lens 1602, which individually focuses each of the separated beams onto one of the three detectors, each of which is arranged for measuring the intensity of the transmitted light.

With regards to reflected light optics 1662, the reflected light beams after reflecting off of substrate 1612 are collected by objective lens 1690, which then directs the beams towards telescope 1688. Before reaching telescope 1688, the beams also pass through a quarter wave plate 1604. In general terms, objective lens 1690 and telescope 1688 manipulate the collected beams in a manner that is optically reverse in relation to how the incident beams are manipulated. That is, objective lens 1690 re-collimates the beams, and telescope 1688 reduces their size. When the beams leave telescope 1688, they continue (backwards) until they reach beam splitter cube 1682. Beam splitter 1682 is configured to work with quarter wave-plate 1604 to direct the beams onto a central path 1606.

The beams continuing on path 1606 are then collected by a first reflected lens 1608, which focuses each of the beams onto a reflected prism 1609, which includes a facet for each of the reflected light beams. Reflected prism 1609 is arranged for repositioning and bending the reflected light beams. Similar to transmitted prism 1610, reflected prism 1609 is used to separate the beams so that they each fall on a single detector in the reflected light detector arrangement 1664. In this embodiment, reflected light detector arrangement 1664 includes three individually distinct detectors. When the beams leave reflected prism 1609, they pass through a second reflected lens 1611, which individually focuses each of the separated beams onto one of these detectors, each of which is arranged for measuring the intensity of the reflected light.

There are multiple inspection modes that can be facilitated by the aforementioned optical assembly. By way of example, the optical assembly can facilitate a transmitted light inspection mode, a reflected light inspection mode, and a simultaneous inspection mode. With regards to the transmitted light inspection mode, transmission mode detection is typically used for defect detection on substrates such as conventional optical masks having transparent areas and opaque areas. As the light beams scan the mask (or substrate 1612), the light penetrates the mask at transparent points and is detected by the transmitted light detectors 1660, which are located behind the mask and which measure the intensity of each of the light beams collected by transmitted light optics 1658 including first transmitted lens 1696, second transmitted lens 1602, spherical aberration lens 1698, and prism 1610.

With regards to the reflected light inspection mode, reflected light inspection can be performed on transparent or opaque substrates that contain image information in the form of chromium, developed photoresist or other features. Light reflected by the substrate 1612 passes backwards along the same optical path as inspection optics 1654, but is then diverted by a polarizing beam splitter 1682 into detectors 1664. More particularly, first reflected lens 1608, prism 1609, and second reflected lens 1611 project the light from the diverted light beams onto detectors 1664. Reflected light inspection may also be used to detect contamination on top of opaque substrate surfaces.

With regards to the simultaneous inspection mode, both transmitted light and reflected light are utilized to determine the existence and/or type of a defect. The two measured values of the system are the intensity of the light beams transmitted through substrate 1612 as sensed by transmitted light detectors 860 and the intensity of the reflected light beams as detected by reflected light detectors 1664. Those two measured values can then be processed to determine the type of defect, if any, at a corresponding point on substrate 1612.

More particularly, simultaneous transmitted and reflected detection can disclose the existence of an opaque defect sensed by the transmitted detectors while the output of the reflected detectors can be used to disclose the type of defect. As an example, either a chrome dot or a particle on a substrate may both result in a low transmitted light indication from the transmission detectors, but a reflective chrome defect may result in a high reflected light indication and a particle may result in a lower reflected light indication from the same reflected light detectors. Accordingly, by using both reflected and transmitted detection one may locate a particle on top of chrome geometry which could not be done if only the reflected or transmitted characteristics of the defect were examined. In addition, one may determine signatures for certain types of defects, such as the ratio of their reflected and transmitted light intensities. This information can then be used to automatically classify defects. U.S. Pat. No. 5,563,702, which issued on Oct. 8, 1996 and is incorporated by reference herein, describes additional details regarding system 1600.

Figure 17:
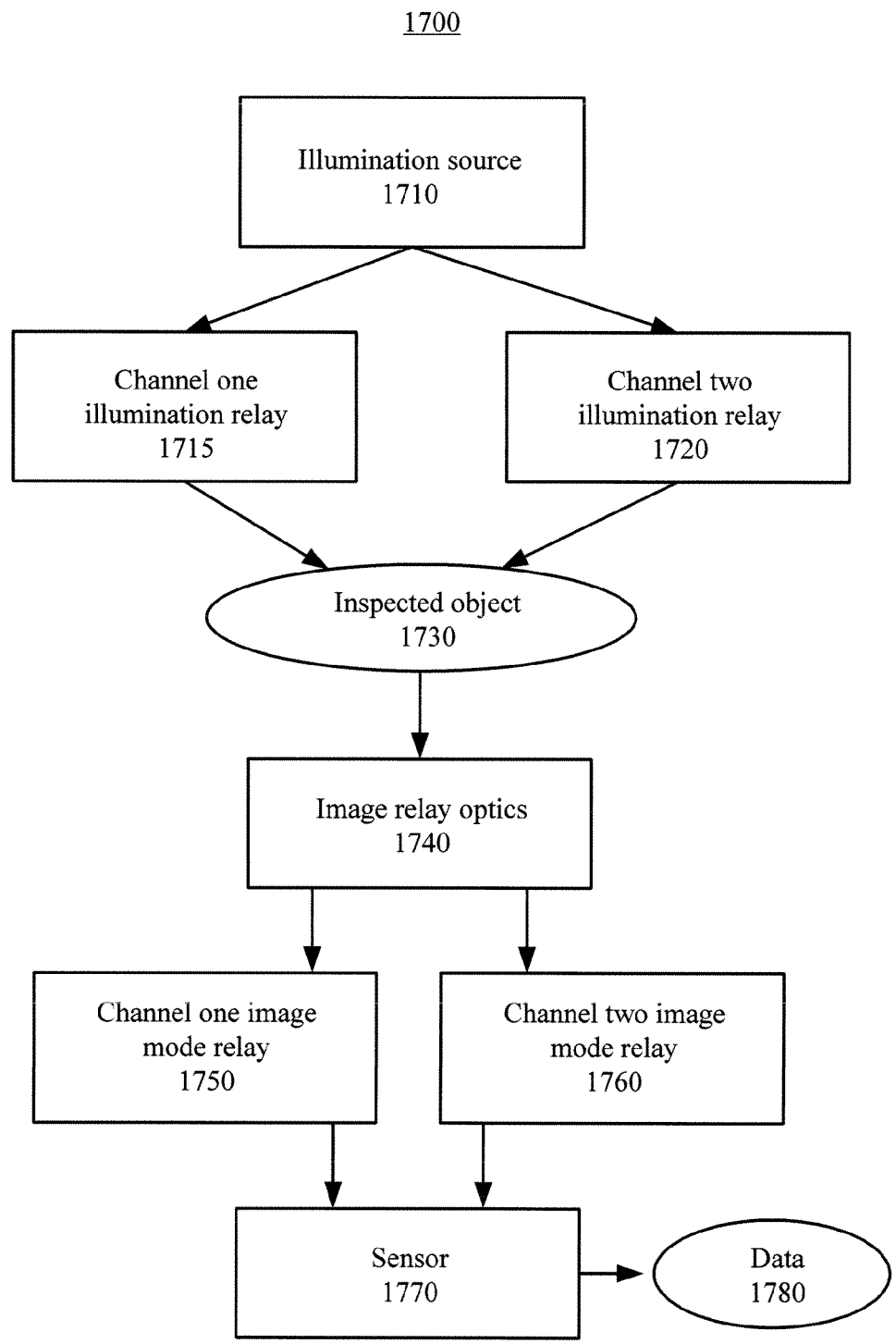
FIG. 17 shows a reticle, photomask or wafer inspection system that simultaneously detects two channels of image or signal on one sensor.

FIG. 17 shows a reticle, photomask or wafer inspection system 1700 that simultaneously detects two channels of image or signal on one sensor 1770. Image sensor 1770 comprises a split-readout image sensor as described above. Illumination source 1710 may incorporate a 193 nm or sub-200-nm laser. The two channels may comprise reflected and transmitted intensity when an inspected object 1730 is transparent (for example a reticle or photomask), or may comprise two different illumination modes, such as angles of incidence, polarization states, wavelength ranges or some combination thereof. Light is directed to inspected object 1730 using channel one illumination relay 1715 and channel two illumination relay 1720.

The inspected object 1730 may be a reticle, a photomask, a semiconductor wafer or other article to be inspected. Image relay optics 1740 can direct the light that is reflected and/or transmitted by inspected object 1730 to a channel one image mode relay 1750 and to a channel two image mode relay 1760. Channel one image mode relay 1750 is tuned to detect the reflection/transmission corresponding to channel one illumination relay 1715, whereas channel two image mode relay sensor 1760 is tuned to detect the reflection/transmission corresponding to channel two illumination relay 1720. Channel one image mode relay 1750 and channel two image mode relay sensor 1760 in turn direct their outputs to sensor 1770. In one embodiment, at least one optical component of sensor 1770, channel one illumination relay 1715, channel two illumination relay 1720, channel one image mode relay 1750, and channel two image mode relay 1760 includes the above-described fluorine-doped silicon oxide film. The data corresponding to the detected signals or images for the two channels is shown as data 1780 and is transmitted to a computer (not shown) for processing.

Other details of reticle and photomask inspection systems and methods that may be configured to measure transmitted and reflected light from a reticle or photomask are described in U.S. Pat. No. 7,352,457, which issued to Kvamme et al. on Apr. 1, 2008, and in U.S. Pat. No. 5,563,702, which issued to Emery et al. on Oct. 8, 1996, both of which are incorporated by reference herein.

Figure 18:
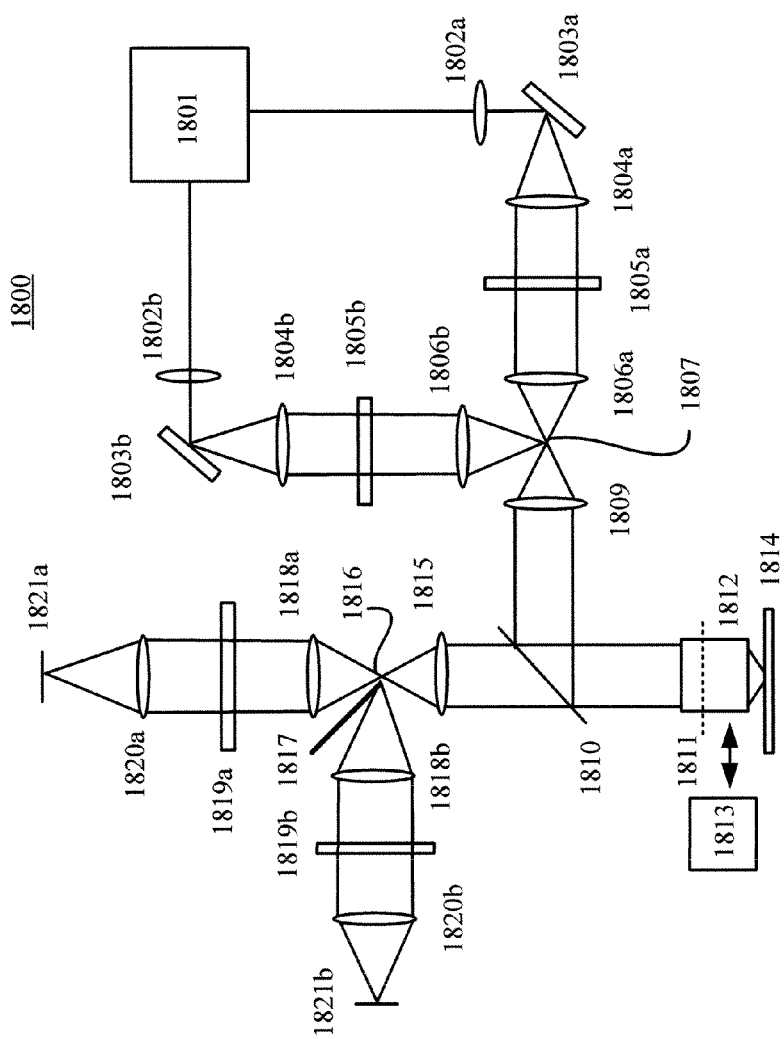
FIG. 18 illustrates an exemplary inspection system including multiple objectives.

FIG. 18 illustrates an exemplary inspection system 1800 including multiple objectives. In system 1800, illumination from a laser source 1801 is sent to multiple sections of the illumination subsystem. A first section of the illumination subsystem includes elements 1802a through 1806a. Lens 1802a focuses light from laser 1801. Light from lens 1802a then reflects from mirror 1803a. Mirror 1803a is placed at this location for the purposes of illustration, and may be positioned elsewhere. Light from mirror 1803a is then collected by lens 1804a, which forms illumination pupil plane 1805a. An aperture, filter, or other device to modify the light may be placed in pupil plane 1805a depending on the requirements of the inspection mode. Light from pupil plane 1805a then passes through lens 1806a and forms illumination field plane 1807.

A second section of the illumination subsystem includes elements 1802b through 1806b. Lens 1802b focuses light from laser 1801. Light from lens 1802b then reflects from mirror 1803b. Light from mirror 1803b is then collected by lens 1804b which forms illumination pupil plane 1805b. An aperture, filter, or other device to modify the light may be placed in pupil plane 1805b depending on the requirements of the inspection mode. Light from pupil plane 1805b then passes through lens 1806b and forms illumination field plane 1807. The light from the second section is then redirected by mirror or reflective surface such that the illumination field light energy at illumination field plane 1807 is comprised of the combined illumination sections.

Field plane light is then collected by lens 1809 before reflecting off a beamsplitter 1810. Lenses 1806a and 1809 form an image of first illumination pupil plane 1805a at objective pupil plane 1811. Likewise, lenses 1806b and 1809 form an image of second illumination pupil plane 1805b at objective pupil plane 1811. An objective 1812 (or alternatively 1813) then takes the pupil light and forms an image of illumination field 1807 at sample 1814. Objective 1812 or objective 1813 can be positioned in proximity to sample 1814. Sample 1814 can move on a stage (not shown), which positions the sample in the desired location. Light reflected and scattered from the sample 1814 is collected by the high NA catadioptric objective 1812 or objective 1813. After forming a reflected light pupil at objective pupil plane 1811, light energy passes beamsplitter 1810 and lens 1815 before forming an internal field 1816 in the imaging subsystem. This internal imaging field is an image of sample 1814 and correspondingly illumination field 1807. This field may be spatially separated into multiple fields corresponding to the illumination fields. Each of these fields can support a separate imaging mode.

One of these fields can be redirected using mirror 1817. The redirected light then passes through lens 1818b before forming another imaging pupil 1819b. This imaging pupil is an image of pupil 1811 and correspondingly illumination pupil 1805b. An aperture, filter, or other device to modify the light may be placed in pupil plane 1819b depending on the requirements of the inspection mode. Light from pupil plane 1819b then passes through lens 1820b and forms an image on sensor 1821b. In a similar manner, light passing by mirror or reflective surface 1817 is collected by lens 1818a and forms imaging pupil 1819a. Light from imaging pupil 1819a is then collected by lens 1820a before forming an image on detector 1821a. Light imaged on detector 1821a can be used for a different imaging mode from the light imaged on sensor 1821b.

The illumination subsystem employed in system 1800 is composed of laser source 1801, collection optics 1802-1804, beam shaping components placed in proximity to a pupil plane 1805, and relay optics 1806 and 1809. An internal field plane 1807 is located between lenses 1806 and 1809.

With respect to laser source 1801, while illustrated as a single uniform block having two points or angles of transmission, in reality this represents a laser source able to provide two channels of illumination, for example a first channel of light energy such as laser light energy at a first frequency which passes through elements 1802a-1806a, and a second channel of light energy such as laser light energy at a second frequency which passes through elements 1802b-1806b. Different light energy modes may be employed, such as bright field energy in one channel and a dark field mode in the other channel.

While light energy from laser source 1801 is shown to be emitted 90 degrees apart, and the elements 1802a-1806a and 1802b-1806b are oriented at 90 degree angles, in reality light may be emitted at various orientations, not necessarily in two dimensions, and the components may be oriented differently than as shown. FIG. 18 is therefore simply a representation of the components employed and the angles or distances shown are not to scale nor specifically required for the design. In one embodiment, at least one of optical component of inspection system 1800 can include the above-described fluorine-doped silicon oxide film.

Elements placed in proximity to pupil plane 1805 may be employed in the current system using the concept of aperture shaping. Using this design, uniform illumination or near uniform illumination may be realized, as well as individual point illumination, ring illumination, quadrapole illumination, or other desirable patterns.

Various implementations for the objectives may be employed in a general imaging subsystem. A single fixed objective may be used. The single objective may support all the desired imaging and inspection modes. Such a design is achievable if the imaging system supports a relatively large field size and relatively high numerical aperture. Numerical aperture can be reduced to a desired value by using internal apertures placed at the pupil planes 1805a, 1805b, 1819a, and 1819b.

Multiple objectives may also be used as shown in FIG. 18. For example, although two objectives 1812 and 1813 are shown, any number is possible. Each objective in such a design may be optimized for each wavelength produced by laser source 1801. These objectives 1812 and 1813 can either have fixed positions or be moved into position in proximity to the sample 1814. To move multiple objectives in proximity to the sample, rotary turrets may be used as are common on standard microscopes. Other designs for moving objectives in proximity of a sample are available, including but not limited to translating the objectives laterally on a stage, and translating the objectives on an arc using a goniometer. In addition, any combination of fixed objectives and multiple objectives on a turret can be achieved in accordance with the present system.

The maximum numerical apertures of this configuration may approach or exceed 0.97, but may in certain instances be higher. The wide range of illumination and collection angles possible with this high NA catadioptric imaging system, combined with its large field size allows the system to simultaneously support multiple inspection modes. As may be appreciated from the previous paragraphs, multiple imaging modes can be implemented using a single optical system or machine in connection with the illumination device. The high NA disclosed for illumination and collection permits the implementation of imaging modes using the same optical system, thereby allowing optimization of imaging for different types of defects or samples.

The imaging subsystem also includes intermediate image forming optics 1815. The purpose of the image forming optics 1815 is to form an internal image 1816 of sample 1814. At this internal image 1816, a mirror 1817 can be placed to redirect light corresponding to one of the inspection modes. It is possible to redirect the light at this location because the light for the imaging modes are spatially separate. The image forming optics 1818 (1818a and 1818b) and 1820 (1820a and 1820b) can be implemented in several different forms including a varifocal zoom, multiple afocal tube lenses with focusing optics, or multiple image forming mag tubes. U.S. Published Application 2009/0180176, which published on Jul. 16, 2009 and is incorporated by reference herein, describes additional details regarding system 1800.

The various embodiments of the structures and methods of this invention that are described above are illustrative only of the principles of this invention and are not intended to limit the scope of the invention to the particular embodiments described. For example, although the above-described fluorine-doped silicon oxide film can be used in image sensors for sensing EUV radiation, this film can also be used in sensors for sensing, deep ultraviolet (DUV), vacuum ultraviolet (VUV), and charged particles. Also, although silicon oxide is described for the embodiments above, in other embodiments, a doped silicon oxide can be used (e.g. using hydrogen or Deuterium). Thus, the invention is limited only by the following claims and their equivalents.

The invention claimed is:

1. An optical component comprising:
 a substrate; and
 a fluorine-doped silicon oxide film formed on the substrate, the fluorine-doped silicon oxide film having a thickness of approximately 1-4 nm and having a fluorine concentration of 0.1% to 5%,
 wherein the thickness and the fluorine concentration of the fluorine-doped silicon oxide film are configured to minimize absorption of energy from radiation having a wavelength below 245 nm.

2. The optical component of claim 1, wherein the optical component forms part of a charge-coupled device (CCD) or a time delay integration (TDI) CCD.

3. The optical component of claim 1, wherein the substrate comprises a material consisting of at least one of boron, silicon nitride, rhodium, titanium oxide, ruthenium and niobium oxide, and
 wherein the fluorine-doped silicon oxide film is adhered to the material.

4. The optical component of claim 1, wherein the substrate comprises a multilayer mirror comprising molybdenum and silicon disposed in alternating layer.

5. The optical component of claim 1, further comprising a boron layer disposed between the fluorine-doped silicon oxide film and the substrate.

6. The optical component of claim 1, wherein the fluorine-doped thin film is configured to have at least one of a hardness greater than 6.5 GPa and a Young's modulus greater than 60 GPa.

7. An anti-reflective coating (ARC) for an optical component operable with at least one of deep ultraviolet (DUV) radiation, vacuum ultraviolet (VUV) radiation, extreme ultraviolet (EUV) radiation, and charged particles, the ARC comprising:
 a multilayer substrate including molybdenum and silicon disposed in alternating layers; and
 a fluorine-doped silicon oxide film formed on the substrate, the fluorine-doped silicon oxide film having a thickness of approximately 1-10 nm and having a fluorine concentration of 0.1% to 5%.

8. The ARC of claim 7, wherein the optical component is a beam splitter, a mirror, a detector, or a sensor.

9. The optical component of claim 7, wherein the fluorine-doped thin film is configured to have at least one of a hardness greater than 6.5 GPa and a Young's modulus greater than 60 GPa.

10. A method of fabricating a protective film for an optical component, the method comprising:
performing a thin film deposition on a silicon substrate to form an oxide; and
introducing fluorine as a dopant during the thin film deposition such that a fluorine-doped silicon oxide film is generated on the oxide, the fluorine-doped silicon oxide film having a thickness of approximately 1-10 nm and having a fluorine concentration of 0.1% to 5% m,
wherein said introducing fluorine includes generating atomic fluorine.

11. The method of claim 10, wherein said generating atomic fluorine includes dissociating fluorine gas.

12. The method of claim 10, wherein said performing thin film deposition is one of oxidation, deep ultraviolet oxidation, sol gel methods, ion-assisted deposition, ion beam sputtering, chemical vapor deposition (CVD), plasma enhanced CVD, plasma deposition, thermal evaporation, and electron beam evaporation.

* * * * *